(12) United States Patent
Phaneuf et al.

(10) Patent No.: US 7,897,918 B2
(45) Date of Patent: Mar. 1, 2011

(54) SYSTEM AND METHOD FOR FOCUSED ION BEAM DATA ANALYSIS

(75) Inventors: Michael William Phaneuf, Ottawa (CA); Michael Anthony Anderson, Nepean (CA); Ken Guillaume Lagarec, Gatineau (CA)

(73) Assignee: DCG Systems, Fremont, CA (US)

(*) Notice: Subject to any disclaimer, the term of this patent is extended or adjusted under 35 U.S.C. 154(b) by 623 days.

(21) Appl. No.: 11/667,789

(22) PCT Filed: Nov. 15, 2005

(86) PCT No.: PCT/CA2005/001733
§ 371 (c)(1),
(2), (4) Date: Dec. 3, 2007

(87) PCT Pub. No.: WO2006/050613
PCT Pub. Date: May 18, 2006

(65) Prior Publication Data
US 2009/0135240 A1    May 28, 2009

(51) Int. Cl.
*G21K 5/02* (2006.01)
(52) U.S. Cl. ............... 250/309; 250/492.1; 250/492.3; 250/492.21; 382/170; 382/171; 382/190; 382/195; 382/199
(58) Field of Classification Search ............... 250/306, 250/307, 309, 310, 311, 491.1, 492.1, 492.2, 250/492.21, 492.3; 382/168, 170, 171, 172, 382/173, 181, 190, 191, 192, 195, 199, 201, 382/276, 282; 702/26, 27, 28, 40; 219/121.12, 219/121.18, 121.19, 121.16
See application file for complete search history.

(56) References Cited

U.S. PATENT DOCUMENTS

| 5,306,907 | A | * | 4/1994 | Nudelman et al. ..... 250/214 VT |
| 5,640,539 | A | | 6/1997 | Goishi et al. |
| 6,579,732 | B2 | * | 6/2003 | Livengood et al. ............ 438/14 |
| 2002/0066863 | A1 | * | 6/2002 | Chao et al. .................. 250/397 |
| 2003/0224543 | A1 | | 12/2003 | Roy et al. |

OTHER PUBLICATIONS

International Search Report for PCT Application No. PCT/CA2005/001733 dated Feb. 17, 2006.
M. Anderson, et al., "A Novel Approach for Enhancing Critical FIB Imaging for Failure Analysis and Circuit Edit Applications," Proceedings from the International Symposium for Testing and Failure Analysis, Nov. 14-18, 2004, pp. 151-156, Worcester, Massachusetts.

* cited by examiner

*Primary Examiner* — Jack I Berman
*Assistant Examiner* — Nicole Ippolito Rausch
(74) *Attorney, Agent, or Firm* — Joseph Bach, Esq.; Nixon Peabody LLP

(57) ABSTRACT

A system and method for improving FIB milling endpointing operations. The methods involve generating real-time images of the area being milled and real-time graphical plots of pixel intensities with an increased sensitivity over native FIB system generated images and plots. The images and plots are generated with raw signal data obtained from the native FIB system. More specifically, the raw signal data is processed according to specific algorithms for generating images and corresponding intensity graphs which can be reliably used for accurate endpointing. In particular, the displayed images will display more visual information regarding changes in milled material, while the intensity graphs will plot aggregate pixel intensity data on a dynamically adjusting scale to dramatically highlight relative changes in milled material.

42 Claims, 14 Drawing Sheets

SYSTEM AND METHOD FOR FOCUSED ION BEAM DATA ANALYSIS

FIELD OF THE INVENTION

The present invention generally relates generally to charged particle beam systems. In particular, the present invention relates to an apparatus and system for processing signal data from focused ion beam FIB systems.

BACKGROUND OF THE INVENTION

Focused Ion Beam (FIB) microscope systems have been produced commercially since the mid 1980's, and are now an integral part of rapidly bringing semiconductor devices to market. FIB systems produce a narrow, focused beam of charged particles, and scan this beam across a specimen in a raster fashion, similar to a cathode ray tube. Unlike the scanning electron microscope, whose charged particles are negatively charged electrons, FIB systems use charged atoms, hereinafter referred to as ions, to produce their beams. These ions are, in general, positively charged.

These ion beams, when directed onto a semiconductor sample, will eject secondary electrons, secondary ions ($i^+$ or $i^-$), and neutral molecules and atoms from the exposed surface of the sample. By moving the beam across the sample and controlling various beam parameters such as beam current, spot size, pixel spacing, and dwell time, the FIB can be operated as an "atomic scale milling machine," for selectively removing materials wherever the beam is placed. The dose, or amount of ions striking the sample surface, is generally a function of the beam current, duration of scan, and the area scanned. The ejected particles can be sensed by detectors, and then by correlating this sensed data with the known beam position as the incident beam interacts with the sample, an image can be produced and displayed for the operator.

FIG. 1 is a schematic of a typical FIB system. FIB system 10 includes an evacuated envelope 11 having an upper neck portion 12 within which are located a liquid metal ion source 14 and a focusing column 16 including extractor electrodes and an electrostatic optical system. Ion beam 18 passes from source 14 through column 16 and between electrostatic deflection means schematically indicated at 20 toward sample 22, which comprises, for example, a semiconductor device positioned on movable X-Y stage 24 within lower chamber 26. An ion pump 28 is employed for evacuating neck portion 12. The chamber 26 is evacuated with turbomolecular and mechanical pumping system 30 under the control of vacuum controller 32. The vacuum system provides within chamber 26 a vacuum of between approximately $1\times10$ E-7 Torr and $5\times10$ E-4 Torr. If an etch assisting, an etch retarding gas, a deposition precursor gas, or some other reactive or non reactive gas is used, the chamber background pressure may rise, typically to about $1\times10$ E-5 Torr.

High voltage power supply 34 is connected to liquid metal ion source 14 and to appropriate electrodes in focusing column 16 and directing the ion beam. Deflection controller and amplifier 36, operated in accordance with a prescribed pattern provided by pattern generator 38, is coupled to deflection plates 20. A charged particle multiplier detector 40 detects secondary ion or electron emission for imaging, is connected to video circuit and amplifier 42, the latter supplying drive for video monitor 44 also receiving deflection signals from controller 36. A door 48 is provided for inserting sample 22 onto stage 24, which may be heated or cooled. Focused ion beam systems are commercially available from various companies, but the system shown in FIG. 1 represents one possible FIB system configuration.

During any beam raster operation executed by FIB system 10, which includes imaging, milling, gas assisted etching or deposition, the FIB beam deflection software and hardware deflects the beam in a preset pattern across the surface, generally referred to as rastering. At each preset location, the beam is left to dwell for a given period of time before moving to the next point in the raster. At its simplest, a raster pass consists of deflecting the beam at fixed increments along one axis from a start point to an end point, dwelling for a fixed dwell time at each point. At the end of a line, the beam waits a fixed retrace time before moving an increment in a second axis. The beam may return to the start point in the first axis and begin again, or may begin "counting down" the first axis from the point it had just reached (depending on whether the raster type is raster (the former) or serpentine (the latter). This process continues until all increments in both axes have occurred, and the beam has dwelled at all points in the scan.

It is well understood by those of skill in the art that FIB systems are used to perform microsurgery operations for executing design verification or to troubleshoot failed designs. This can involve physically "cutting" metal lines or selectively depositing metallic lines for shorting conductors together. Hence, FIB system technologies can enable prototyping and design verification in a matter of days or hours rather than weeks or months as re-fabrication would require. This FIB "rapid prototyping" is frequently referred to as "FIB device modification", "circuit editing" or "microsurgery." Due to its speed and usefulness, FIB microsurgery has become crucial to achieving the rapid time-to-market targets required in the competitive semiconductor industry.

While FIB microsurgery is useful for semiconductor circuit design verification, the successful use of this tool relies on the precise control of the milling process. Current integrated circuits have multiple alternating layers of conducting material and insulating dielectrics, with many layers containing patterned areas. Hence the milling rate and effects of ion beam milling can vary vastly across the device.

Unfortunately, a FIB operator is responsible for halting the milling process when a metal line of interest has been sufficiently exposed or completely cut, a process known as "endpointing". Endpointing is done based on operator assessment of image or graphical information displayed on a user interface display of the FIB system. In most device modification operations, it is preferable to halt the milling process as soon as a particular layer is exposed. Imprecise endpointing can lead to erroneous analysis of the modified device. Older FIB systems operating on current state-of-the-art semiconductor devices do not provide image and graphical information with a sensitivity that is usable by the operator. This is due in part to the fact that older FIB systems will have imaging systems originally optimized for older generation semiconductor devices.

In particular, as semiconductor device features continue to decrease in size from sub-micron to below 100 nm, it has become necessary to mill smaller and higher aspect ratio FIB vias with reduced ion beam current. This significantly reduces the number of secondary electrons and ions available for endpoint detection and imaging. In addition, FIB gas assisted etching introduces a gas delivery nozzle composed of conductive material. This component is grounded to prevent charge build up during ion beam imaging or milling. The proximity of the nozzle to the sample surface creates a shielding effect which reduces the secondary electron detection level.

FIB operators typically rely on a real-time image of the area being milled and a graphical data plot in real time, to determine proper endpoint detection. Generally, the FIB operator is visually looking for changes in brightness of the milled area to qualitatively determine endpoint detection. Such changes may indicate a transition of the mill through different materials, such as a metal/oxide interface.

FIG. 2 illustrates an example of a problem with real-time imaging provided by current FIB systems. The FIB system generates data at each dwell point, but whether the native microsurgery software displays this data depends on a number of factors, including the particular field of view (FOV, which is directly related to the chosen magnification factor of the microscope) the FIB is operating at, the spacing of the desired increments along each axis, the dwell time per point, etc. Take for example a square mill box 60 having 0.1 µm×0.1 µm dimensions being milled at a 10 µm FOV, indicated by reference number 62. Box 62 represents the viewable area on the monitor of FIB system 10. It is noted that areas 60 and 62 are not to scale. The operator will typically elect to use such a field of view in order to properly determine the position of mill box 60 on the surface of the sample. The imaging area displayed on the user interface monitor is slightly under 1024 pixels×1024 pixels, but the FOV is divided up into exactly 1024 pixels in both the x and y axes. At this FOV, each screen pixel will be under 10 nm×10 nm, and a 0.1 µm square box (100 nm×100 nm) occupying 10 pixels×10 pixels on the screen, for 100 pixel "data points" in total that are visible to the user. If the mill box parameters are set to a spacing of 0.005 µm×0.005 µm (5 nm), then in a single pass the FIB will actually dwell at (100 nm/5 nm)+1=21 points in each box axis, generating 441 dwell points of information. Under these conditions, the FIB will display the information it generates across a region that is only 1% of the width of its display area (0.1 µm box width/10 µm FOV).

Due to the small image area and a reduced level of electron detection, the real-time image may not provide any value for the FIB operator for endpoint detection since changes in the image would be very difficult to visually detect. Furthermore, some FIB systems execute data preprocessing, such as dithering, which in fact reduces an operators' level of confidence in determining proper endpointing for state-of-the-art semiconductor devices.

To supplement the real-time imaging, a pixel intensity versus dose/depth graph is plotted in real-time during a milling operation. It is noted that both the milled image and the graph would be provided on the user monitor at the same time. FIG. 3 is a graphical plot typically relied upon by FIB operators to determine proper endpoint detection. In present example, the graphical plot is generated from the small mill box 62 in FIG. 2. The graph plots an 8-bit pixel intensity (0-255) against dose/depth, during microsurgery of a state-of-the-art semiconductor device. The plot is intended to provide the operator with an empirical indicator of endpoint detection. Typically, a transition between metal and oxide should be clearly illustrated in the plot. If the operator is to correctly determine endpoint. One difficulty in the present scheme arises from plotting the data on a fixed scale, such as the 8-bit (0-255) scale found on many instruments, that does not dynamically rescale to show more sensitive changes. A larger difficulty arises from the fact that the present system bases its analysis on the 100 pixel data points described above that result from the fact that the data is displayed on a 10 pixel×10 pixel area, even though the actual number of dwell points is 21×21=441. Thus, less than one quarter of the available data is processed by the current system, making small transitions in intensity even smaller. These two factors combine to decrease the sensitivity of the present system.

Accordingly, there is a lower probability of successful endpoint detection by the FIB operator, and a lower probability of successful design verification, leading to no data on the success of a new design, or worse erroneous results that may lead to incorrect design changes being propagated into the final device. New FIB systems calibrated for state-of-the-art devices may be available, but the cost of replacing older FIB systems is prohibitive. Modification of the FIB system firmware or hardware is generally prohibited, since FIB system modification voids certification of the system and any manufacturer warranties.

In SIMS (secondary ion mass spectrometry) systems for analyzing or detecting chemicals in a semiconductor material, software has been developed for enhancing images to highlight areas where a specific chemical is detected. However, SIMS operation does not require endpointing. In fact, a SIMS operator can arbitrarily determine when the process should stop without any concern for what layers of material have been destroyed by the ion beam. In Microsurgery, there is typically a requirement that the device remain electrically active after the circuit editing has been performed. In SIMS, not such requirement exists, and in fact it is often a requirement that SIMS be performed on a device that is not complete (typically just a bare silicon die with no conductor layers fabricated) and therefore cannot operate. In fact, for semiconductor devices, the emission of particles from destroyed structures required for determining their chemical compositions. In contrast for example, FIB endpointing operations require precise control over when the mill should stop so as not to destroy a specific structure.

Additionally, as devices become more complex, the number of operations required to perform successful microsurgery typically increases, as do the complexity of these operations. It is generally required and always desirable that all elements of the microsurgery (i.e. cuts of certain interconnect and joins between other interconnect) function correctly. After a microsurgery has been performed, it is necessary to test the device to determine if the design change implemented by the microsurgery has had the desired result. The method of developing test programs and test systems is well known in the industry. If the device does not function as expected, it is not uncommon for the test systems to produce data that can be analyzed to determine what is not functioning correctly.

The difficulty arises in more complex circuit edit tasks, in determining if the unexpected function is due to a flaw in the design or an error in how the design was implemented through microsurgery. At present, the microsurgery operator must rely on a few images digitally captured during the course of the circuit edit, and their own memory as to what might have gone wrong that could have produced the result observed. As time passes and other microsurgery tasks are performed it is difficult for the operator to recall every element of a particular surgery, and even if the test results are obtained very quickly after completion of the surgery, it is not possible for all operators to recall all aspects of the task.

It is, therefore, desirable to provide a method for improving endpoint detection in FIB systems.

SUMMARY OF THE INVENTION

It is an object of the present invention to obviate or mitigate at least one disadvantage of previous endpoint detection schemes. In particular, it is an object of the present invention to generate images and endpoint graphs having improved sensitivity to changes.

In a first aspect, the present invention provides a method for enhancing endpointing determination in a charged particle beam system operation involving material modification. The method includes receiving dwell point intensity values, processing the dwell point intensity values, and plotting a summation of the dwell point intensity values. More specifically, the step of receiving includes receiving dwell point information from each frame generated by the CPB system, where the information includes dwell point intensity values. The step of processing includes processing the dwell point intensity values of a first region of interest of a first number of frames to derive raster data, and when the first region of interest is defined, mapping the raster data to an image palette and displaying the resultant raster image. The step of plotting includes plotting a summation of the dwell point intensity values of a second region of interest of a second number of frames on an endpoint graph versus charged particle dose or rastering time, when the second region of interest is defined.

According to embodiments of the present aspect, the raster data is mapped and displayed after one of a predetermined time interval, a predetermined dose increment or a predetermined number of frames, and the summed dwell point intensity values are plotted after one of a predetermined time interval, a predetermined dose increment or a predetermined number of frames. The first number can be automatically calculated to obtain raster images having an appearance of real-time responsiveness to changes and improved signal to noise ratio over a live raster image. Each raster data can be processed by summing the dwell point intensity values of the first number of frames, and rescaling the raster data from a selected minimum value to a selected maximum value over a predetermined scale. Values in the raster data less than or equal to the selected minimal value become a new minimum value and values in the raster data greater than or equal to the selected maximum value become a new maximum value, and another image palette can be mapped that ranges from the new minimum value to the new maximum value. The resultant scaled raster image can then be displayed. In a preferred embodiment, the raster data mapped to the image palette remains unchanged until one of a predetermined time interval has elasped, a predetermined dose increment is received or a predetermined number of frames has elapsed.

In further embodiments, the method includes a step of generating a differential display image from a difference between current raster data and a predetermined number of previous raster data, wherein each of the predetermined number of previous raster data is weighted by decreasing percentages. The image palette can include multiple colors which are effective for increasing the perception of changes in the resultant raster image compared to a greyscale palette.

In yet another embodiment, the method can include a step of determining if the charged particle beam system is in an imaging mode, thereby classifying the frame information as corresponding to an imaging mode operation for imaging a field of view or a subset of the field of view. The image corresponding to frame information for the imaging mode operation is displayed in an imaging mode window and the raster image is displayed in a raster mode window. In a preferred aspect of the present embodiment, the imaging mode window is brought to the foreground if the frame information is classified as an imaging mode operation, and the raster mode window is brought to the foreground if the frame information is classified as a raster operation. Alternately, the raster image can be scaled and superimposed in the correct location on the imaging mode window.

In a further embodiment, the steps of processing and plotting are repeated two or more times for a plurality of regions of interest and a variable number of frames, or the step of processing can be repeated two or more times for the first region of interest and a variable number of frames and image palettes. Alternately, the step of plotting can be executed for only the region of interest with the smallest area.

In another embodiment of the present aspect, the method can include generating thumbnail data from the raster data by scaling the raster data after one of a predetermined time interval, a predetermined dose increment or a predetermined number of frames, for subsequent storage. The method can include storing one or more of the image palette, a charged particle beam current, a delivered charged particle dose, a rastering time and the endpoint graph data corresponding to the thumbnail data. The endpoint graph and at least one thumbnail image constructed by applying the image palette to at least one of the thumbnail data can be displayed, and each thumbnail image can be cross-referenced to one corresponding intensity value on the endpoint graph such that selecting a value on the endpoint graph causes the nearest cross-referenced thumbnail to be displayed. The method can include constructing a cross-section image by defining a line segment in the plane of the thumbnail data, and generating a row of the cross-section image by analyzing the intensity values along the line segment of each thumbnail datum and stacking each row sequentially from top to bottom, such that the horizontal axis of the cross-section image corresponds to space and the vertical axis corresponds to time or dose. In a preferred aspect, the step of analyzing can include one of averaging or integrating the intensity values along a vector perpendicular to the line segment for a predetermined distance on either side of the line segment. The method can include a step of displaying the endpoint graph, at least one thumbnail image constructed by applying a predetermined image palette to at least one of the thumbnail datum, and the cross section image, where each thumbnail image is cross-referenced to one corresponding intensity value on the endpoint graph and one row of the cross-section image. Selecting a point on the endpoint graph causes the nearest cross-referenced thumbnail image to be displayed and the cross-referenced row of the cross-section image to be indicated, or selecting a row on the cross-section image causes the cross-referenced thumbnail image to be displayed and the cross-referenced point on the endpoint graph to be indicated.

In a further aspect, the first region of interest is set to be an area occupied by at least one raster shape in the frame, or the first region of interest is set to be a subset of an area occupied by at least one raster shape in the frame. The subset can be selected to exclude all dwell points within a predetermined distance from a perimeter of the at least one raster shape. The at least one raster shape can have at least one internal perimeter, where the subset can be selected to further exclude all dwell points within another predetermined distance from the at least one internal perimeter. The first region of interest can be set to be a union of the areas occupied by at least two raster shapes overlapping in the frame, and the first region of interest can be further selected to exclude all dwell points within a predetermined distance from a perimeter of the at least one raster shape.

In yet another aspect, the second region of interest is set to be an area occupied by at least one raster shape in the frame, or the second region of interest is set to be a subset of an area occupied by at least one raster shape in the frame. The subset can be selected to exclude all dwell points within a predetermined distance from a perimeter of the at least one raster shape. The at least one raster shape can have at least one internal perimeter, where the subset can be selected to further exclude all dwell points within another predetermined distance from the at least one internal perimeter. The second region of interest can be set to be a union of the areas occupied by at least two raster shapes overlapping in the frame, and the second region of interest can be further selected to exclude all dwell points within a predetermined distance from a perimeter of the at least one raster shape.

In other embodiments of the present aspect, the information from each frame generated by the CPB system, and CPB system operating parameters can be stored for subsequent retrieval and processing according to the steps of processing and plotting. The step of plotting can include re-scaling the y-axis to a new range which includes all summed dwell point intensity values over the range of the x-axis displayed on the endpoint graph, for increasing ease of perception in determining when changes in the summed dwell point intensity values are occurring.

In a second aspect, the present invention provides a method for imaging in a charged particle beam system operation involving material modification. The method includes receiving dwell point intensity values, and processing the dwell point intensity values. More specifically, the step of receiving includes receiving dwell point information from each frame generated by the CPB system, the information including dwell point intensity values. The step of processing includes processing the dwell point intensity values of a region of interest of a number of frames to derive raster data, mapping the raster data to an image palette and displaying the resultant raster image stretched by a first predetermined factor greater than zero in a first axis and by a second predetermined factor greater than zero in a second axis.

In an embodiment of the present aspect, the first predetermined factor and the second predetermined factor can be equal or the second predetermined factor can be greater than the first predetermined factor.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
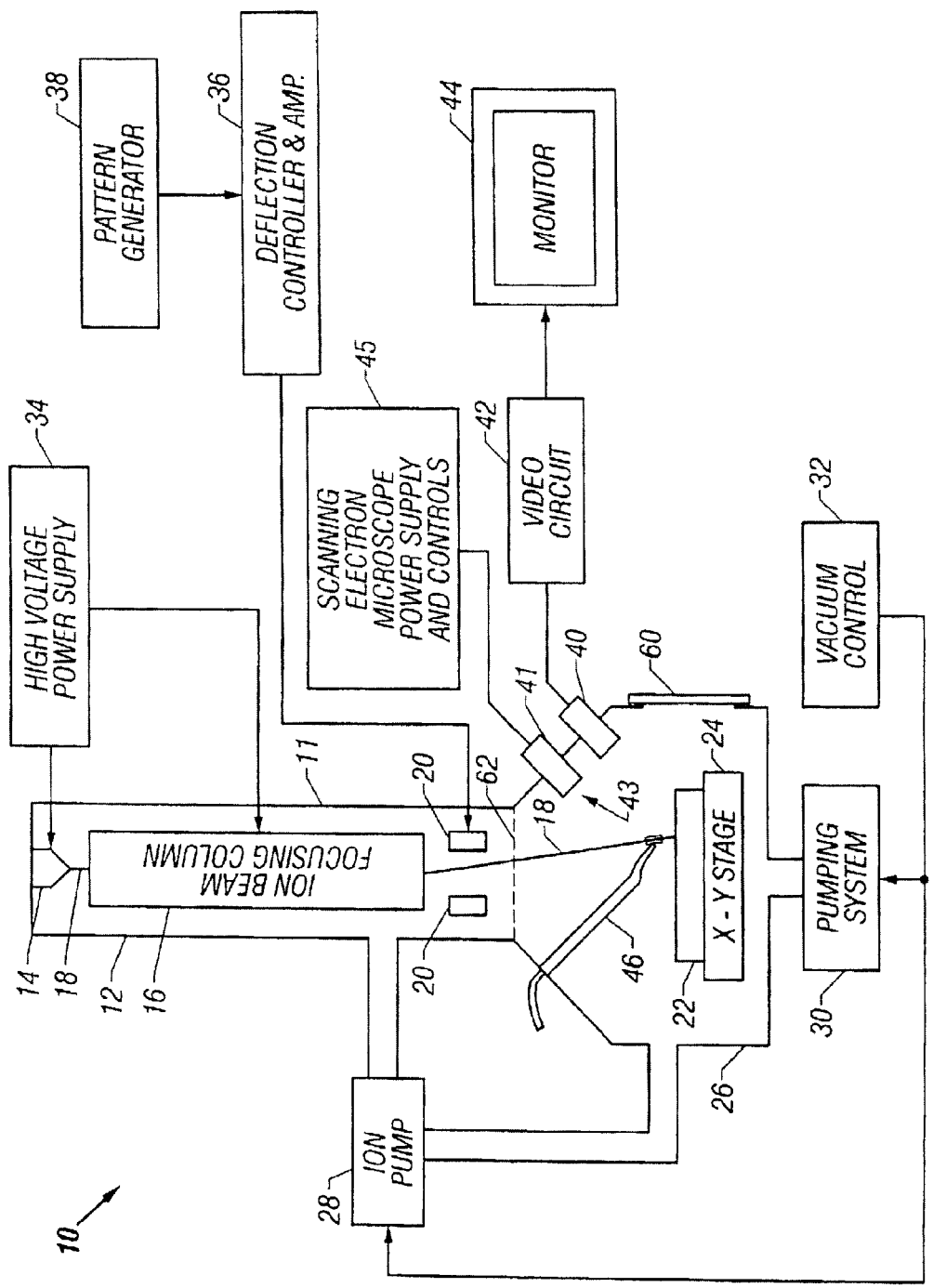
FIG. 1 is a schematic of a FIB system of the prior art.

Generally, the present invention provides methods for improving FIB milling endpointing operations. The methods involve generating real-time images of the area being milled and real-time graphical plots of pixel intensities with an increased sensitivity over native FIB system generated images and plots. The images and plots are generated with raw signal data obtained from the native FIB system. More specifically, the raw signal data is processed according to specific algorithms for generating images and corresponding intensity graphs which can be reliably used for accurate endpointing. In particular, the displayed images will display more visual information regarding changes in milled material, while the intensity graphs will plot pixel intensity data on a dynamically adjusting scale to dramatically highlight relative changes in milled material, as well as interpreting all dwell point data produced by the system rather than a subset, as in the current state of the art systems. This supplemental information is displayed on the monitor of a FIB analysis station coupled to the native FIB system.

Following are definitions of specific terms and expressions used in the description.

A raster shape is a feature that is rastered by the charged particle beam, typically but not limited to a rectangular area having width W and height H defined in (u,v) coordinates with a starting point (u0,v0) and a raster step size du and dv. A raster shape includes a fixed or variable collection of dwell times for each dwell point, and can include a "mask" used to determine whether a dwell point is rastered or not, and perhaps for how long. A raster shape may also, for example, consist of polygon and line segments each defined in (u,v) coordinates with a starting point (u0,v0) and a raster step size du and dv, along with corresponding dwell and mask information. At its most generic, a raster shape is merely a list of coordinates that are rastered, coupled with information pertaining to how long the beam dwelt at each discretized location. At a higher level, a raster shape may consist of parameterized information such as the W, H, u0, v0, du, dv, dwell mask and dwell time information necessary to reconstruct the expected position of the beam if the index of a given intensity value in a sequence of intensity values is known.

A frame is a collection of dwell point data with a known start and end point comprising intensity values and beam position information in the form of one or more raster shapes. The completion of one frame and the start of another may be triggered from three perspectives: geometry, time or dose. From a geometry perspective, a frame starts when the beam commences rastering the nth pass of the first of a collection of raster shapes and ends when the beam completes rastering the nth pass of the last of a collection of raster shapes. From a time perspective, one frame ends and a new one may begin after a predetermined length of time has elapsed. From a dose perspective, one frame ends and a new one may begin after a predetermined number of charged particles have been directed at a given area of the target.

A Region of Interest (ROI) is a selected subset of the data in a frame that can be defined on an areal or shape basis. A ROI may be constructed arbitrarily or by applying a selection criteria to some or all of the raster shapes in the frame. One example of a selection criteria is "all dwell points within a raster shape except those on the perimeter of the raster shape". Dwell points that occur inside the region of interest are processed; dwell points that occur outside the region of interest are ignored. If a region of interest is not defined all dwell points are ignored, resulting in zero data being processed for that operation. By default, the region of interest is the area occupied by all raster shapes in the frame.

Figure 4:
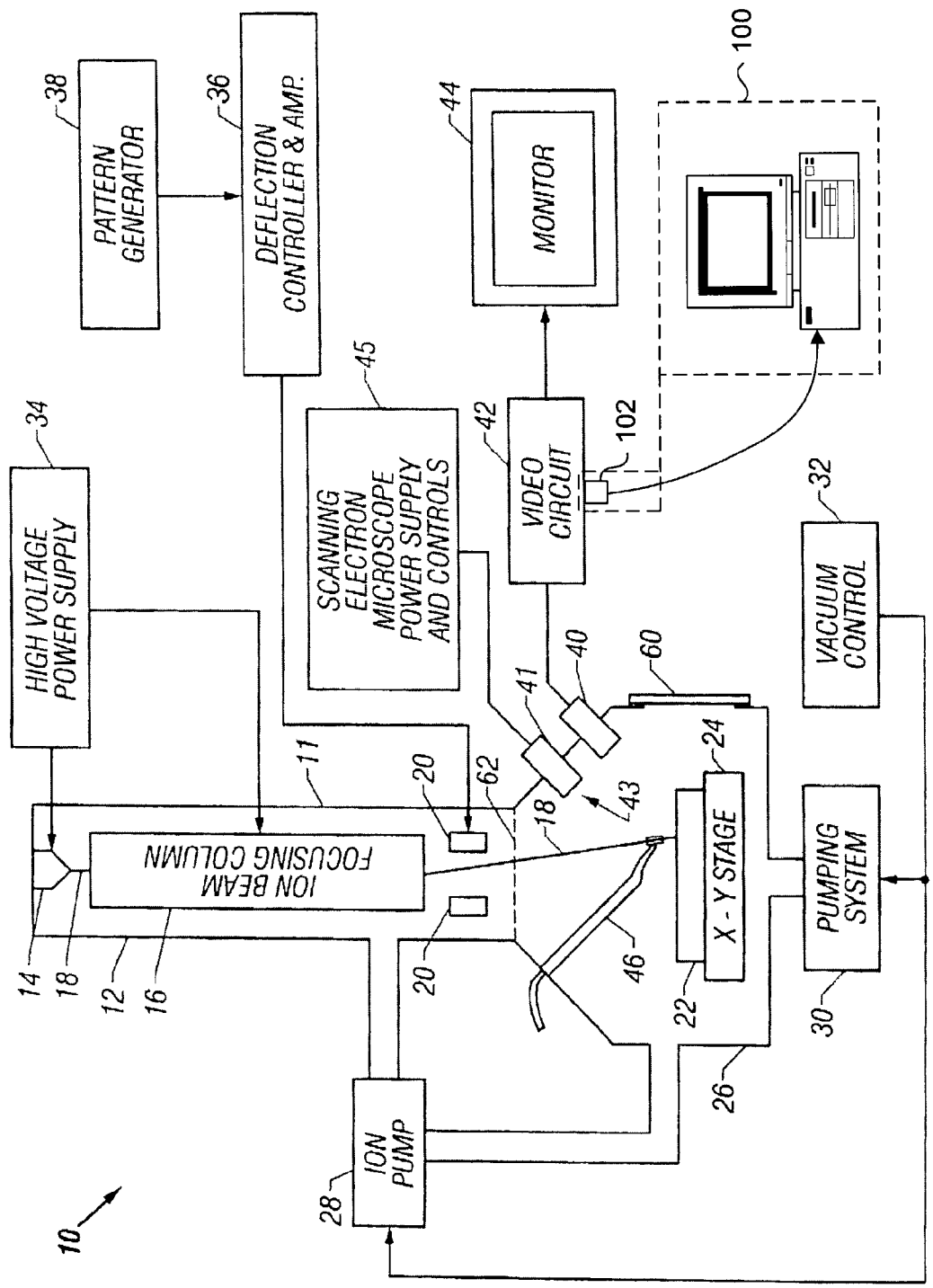
FIG. 4 is a schematic of the FIB system of FIG. 1 with the FIB analysis station according to an embodiment of the present invention.

FIG. 4 is a block diagram showing the general relationship between the FIB system 10 shown in FIG. 1 and a FIB analysis station 100, according to an embodiment of the present invention. FIB analysis station 100 can be a separate system that runs its own image and data processing algorithms independently of FIB system 10, or can be integrated onto the host FIB system. FIB analysis station 100 can be used to "retro-fit" older FIB systems while the functionality of FIB analysis station 100 can be integrated during assembly/design of newer FIB systems. Many FIB systems have an accessible console with removable boards inserted therein to control particular functions of the FIB system 10. It is through one or more of these boards that the pixel data stream is routed. Once the appropriate signal lines are identified, the appropriate hardware interface can be custom configured to mate with the board and "eavesdrop" on the signals. While these signals are fed to other parts of the FIB system 10 during an operation, they are also being received by FIB analysis station 100. The signal data acquired by FIB analysis station 100 includes deflection values, unprocessed x-y coordinate and pixel intensity data sent to the native FIB computer (in some cases a system running the AIX (Advanced Interactive executive by IBM) operating system and microsurgery software supplied by the FIB vendor) and FIB operation parameters sent from the FIB system AIX computer to the beam control circuits.

Preferably, FIB analysis station 100 includes a microprocessor, memory and mass storage, typically embodied as a computer workstation with a monitor, and a FIB system hardware interface 102. In the presently shown embodiment of FIG. 4, a cable is the means for communicating the data to the workstation. However, any transmission means can be used. The FIB system native image processing and the FIB analysis station 100 operate in parallel and independently of each other. The FIB analysis station 100 is passive and does not control operational functions of the FIB system. Hence any FIB system can be retro-fitted once the necessary signals have been identified and tapped. Note that it may be desired that the FIB analysis station interact to provide operational functions, but this is not a requirement.

The FIB analysis station 100 takes advantage of the fact that most FIB systems operate in almost all milling modes as a "contiguous pixel generator". This means that the FIB system, such as FIB system 10, produces a rectangular stream of row and column data for each raster pass, where dwell points in immediately adjacent rows or columns can be expected to have a "neighbor" relationship with each other. This "neighbor" relationship can be exploited in order to improve the image perceived by the user by interpolating between neighboring dwell points in order to enlarge the image (thus creating more pixels in the display than there were dwell points in the mill box) or eliminating peripheral dwell points to reduce spurious edge effects when milling deep vias.

More specifically, FIB system 10 operates in a mode where a mill box is defined in (u,v) space, and the beam steps in increments of du, dv, where (u,v) are orthogonal vectors at some angle to the real world (specimen) space (x,y). A typical mill is a rectangle or polygon, where the beam steps in increments of du and/or dv, dwelling at each point for a predetermined time. Note that one may choose to instruct the FIB to "skip" certain dwell points such that the FIB may scan (u0, v0), (u1,v0), (u2,v0), then skip one dwell point to (u4,v0), for example. Thus most of the time, the FIB rasters by steps of du and/or dv inside a rectangular space defined by (u0, v0) to (W*du, H*dv), potentially skipping some dwell points as instructed. Note also that the actual beam positions generated by the digital scan system may be integer approximations.

Another approach to scanning the beam is to specify a "deflection list" of points consisting of an (x,y) position and the time to dwell at that point (or just a series of (x,y) points, each with a uniform dwell time). This list may be a series of line segments or a totally free-form series of points. One cannot assume, under these circumstances, that the elements in the list map to contiguous points in space. The problem with this type of data is how to display this to the user.

One approach is to define an array of elements (say for example 4096×4096) that maps the total available scan area of the FIB, then determine the "spot size" of the beam, and calibrate that size in terms of how many elements correspond to the diameter of the spot at a given field of view in the FIB (or other charged particle microscope). Thus, if the beam is 10 nm in size, and field of view is 4,096 nm×4,096 nm, each element in the array corresponds to 1×1 nm in specimen space, and the spot size is 10 elements across. One may then choose to fill a circle 10 elements in diameter (or a square, or whatever shape is appropriate), centered at each dwell point's (x,y) location in the element array, with the intensity value from whatever detector(s) are used to generate the signal. A frame under this scheme starts at a known state (perhaps blank, perhaps at whatever data has already been acquired) and is modified by the addition and manipulation of however many circles of data from however many dwell points occur in a predetermined frame interval. Once this frame has been assembled, it (or some subset of it) is passed on to FIB analysis station 100 for manipulation as if it were a typical (u0, v0) to (W*du, H*dv) frame.

As the "deflection list" cannot be assumed to be contiguous, the resulting image may have "gaps" that are not visually appealing when scaled. Treating each dwell point as introducing the same data to a region that is circular and approximately the diameter of the beam (or some function of that diameter, that may take into account, for example, the interaction volume around the beam) still may not produce as visually appealing an image, however it is at least a realistic depiction of what is occurring on the sample and is likely the best option when it cannot be assumed that the data will fall on regular intervals of (du,dv).

In general operation, FIB analysis station 100 acquires the intensity at each dwell point, for each raster pass, regardless of dwell time and the resultant time per raster. This means that in excess of 1,000 FIB rasters (or mill box frames) can occur every second. It is generally understood that the human eye will consider a 24 fps (frames per second) rate to be sufficiently acceptable to give the appearance of smooth motion, and even 20 fps appears smooth when each successive frame contains considerable smoothly varying detail, as is often the case during FIB milling. Thus, at 1000 rasters per second of FIB raster rate it is possible to integrate 50 FIB rasters into a single frame for display and still achieve a display rate of 20 fps. As each dwell point produces an 8-bit intensity value, each dwell point can have intensity values ranging from 0 to 255. Of course, different systems can provide dwell point intensity values greater than 8-bits. Averaged images preserve this range of data, however integrated images can reach many thousand counts per dwell point, allowing the user to adjust the image provided by the FIB analysis station 100 to enhance a particular subset of signal intensity that cannot be resolved in the average image or even on the screen of the FIB system 10. Known graphics processing algorithms can be used to optimize the image, which includes for example optimizing the FIB contrast (effectively the secondary particle detector gain) and brightness base settings as well as adjusting how the FIB analysis station 100 displays this data.

In addition to providing a displayed live, averaged or integrated image superior to the native image provided by FIB system 10, FIB analysis station 100 will calculate the intensity data from each and every raster pass, displaying an endpoint graph plot of both the average intensity (0-255) and integrated intensity at a default interval of 250 ms from all rasters received during the previous interval.

Figure 2:
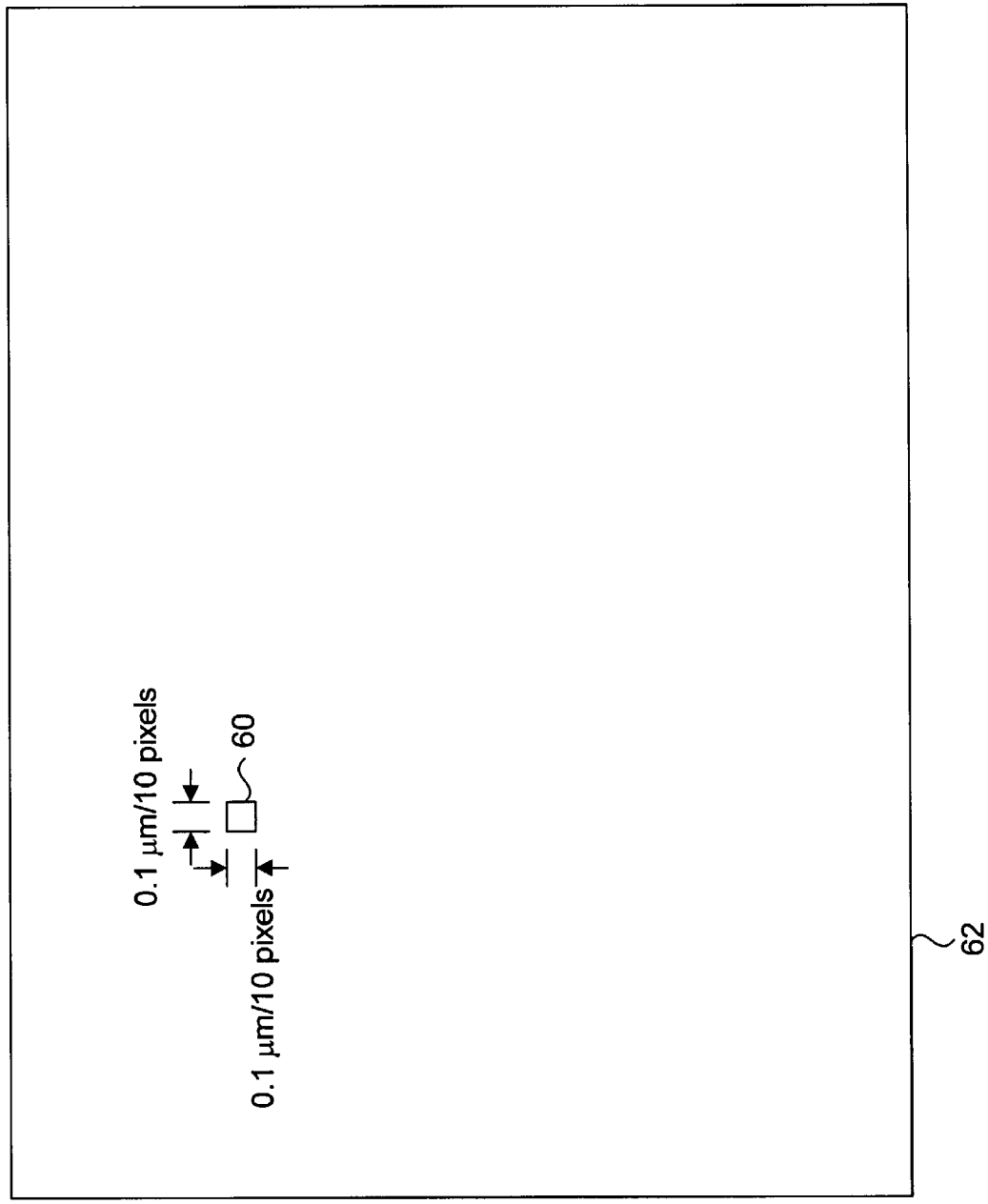
FIG. 2 is an illustration of a field of view from the FIB system of FIG. 1.
Figure 5:
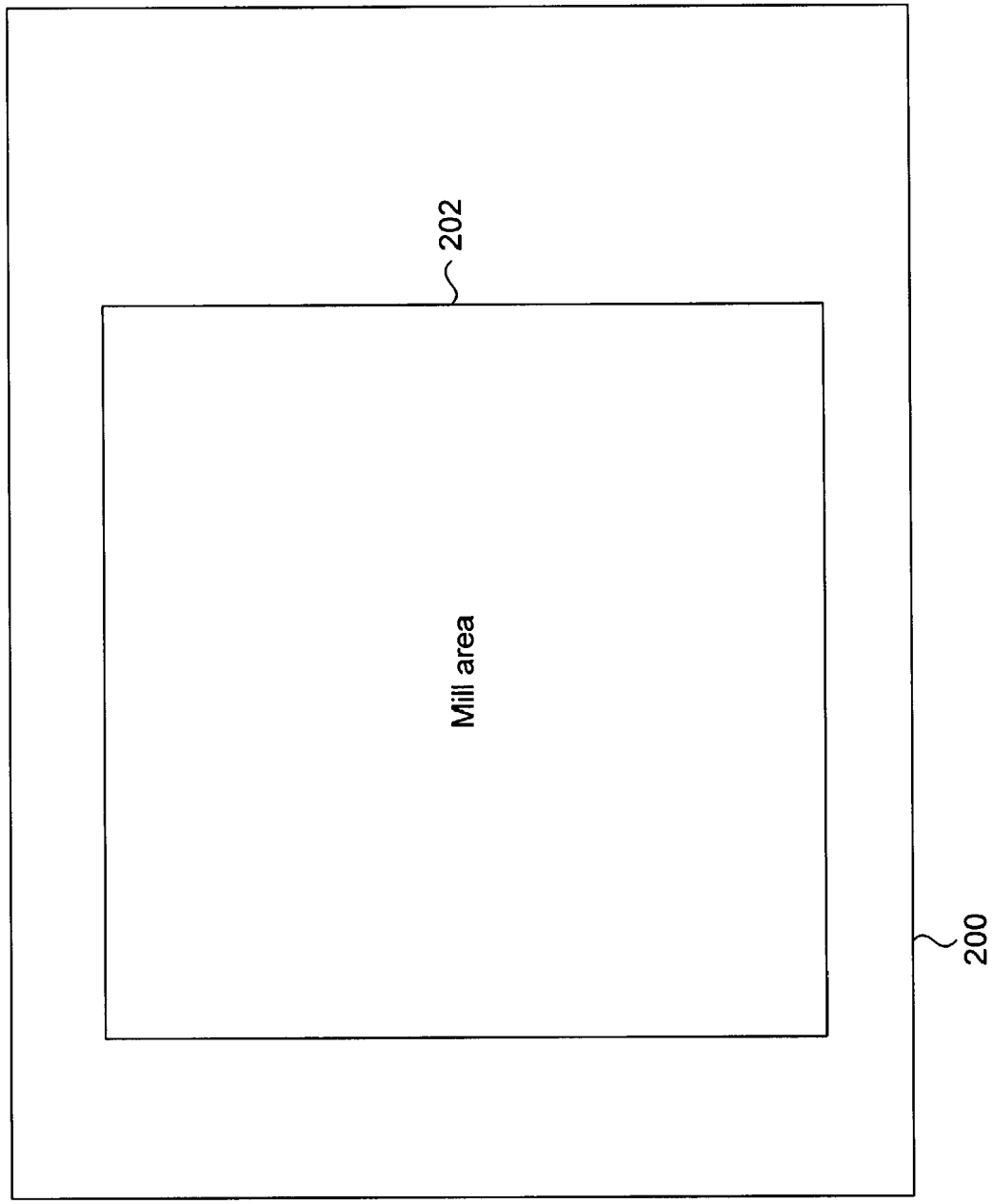
FIG. 5 is an illustration of a field of view from the FIB analysis station shown in FIG. 4.

FIG. 5 illustrates an example zoomed milling area that can be displayed for the user on the monitor of the FIB analysis station 100 according to an embodiment of the invention. Rectangular area 200 represents the viewable screen area of the monitor of FIB analysis station 100. Initially, the monitor of FIB analysis station 100 may look the same as in FIG. 2. However, after image processing the data used for displaying mill box area 62 in FIG. 2, the user can expand the viewable milling area to box 202. With the additional pixel information being displayed, slight visual differences imperceptible in mill box area 62 will be easily seen in mill box area 202, as more ion beam dwell point information can be displayed through many more pixels. In the presently described embodiments, the term "mill box" generally refers to a rectangular box or area, but will refer to any arbitrary shape. As will be discussed later, the data used to generate the viewable milling area in box 202 can be processed to enhance visual endpointing by the operator.

Figure 3:
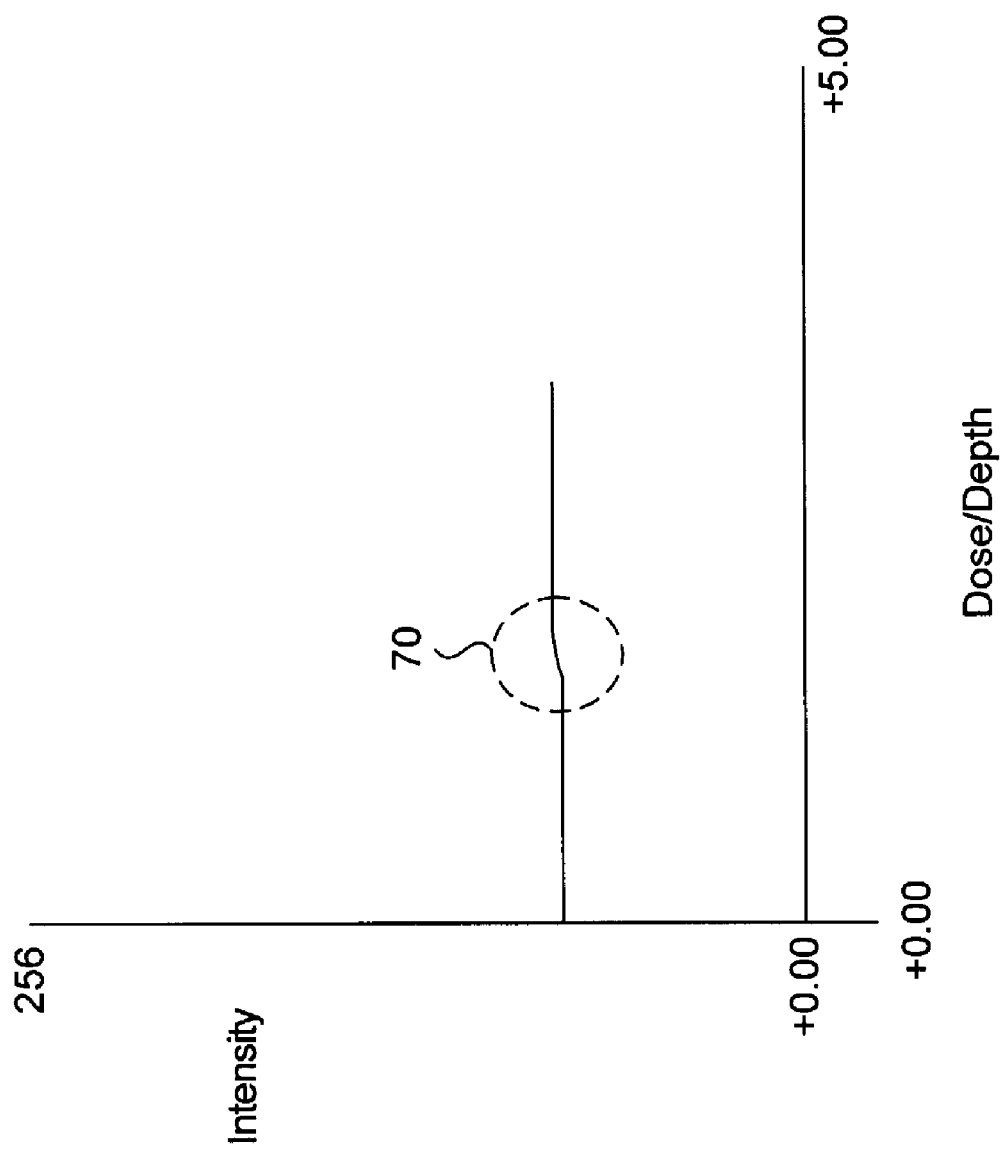
FIG. 3 is a graph of pixel intensity versus dose/depth from the FIB system of FIG. 1.
Figure 6:
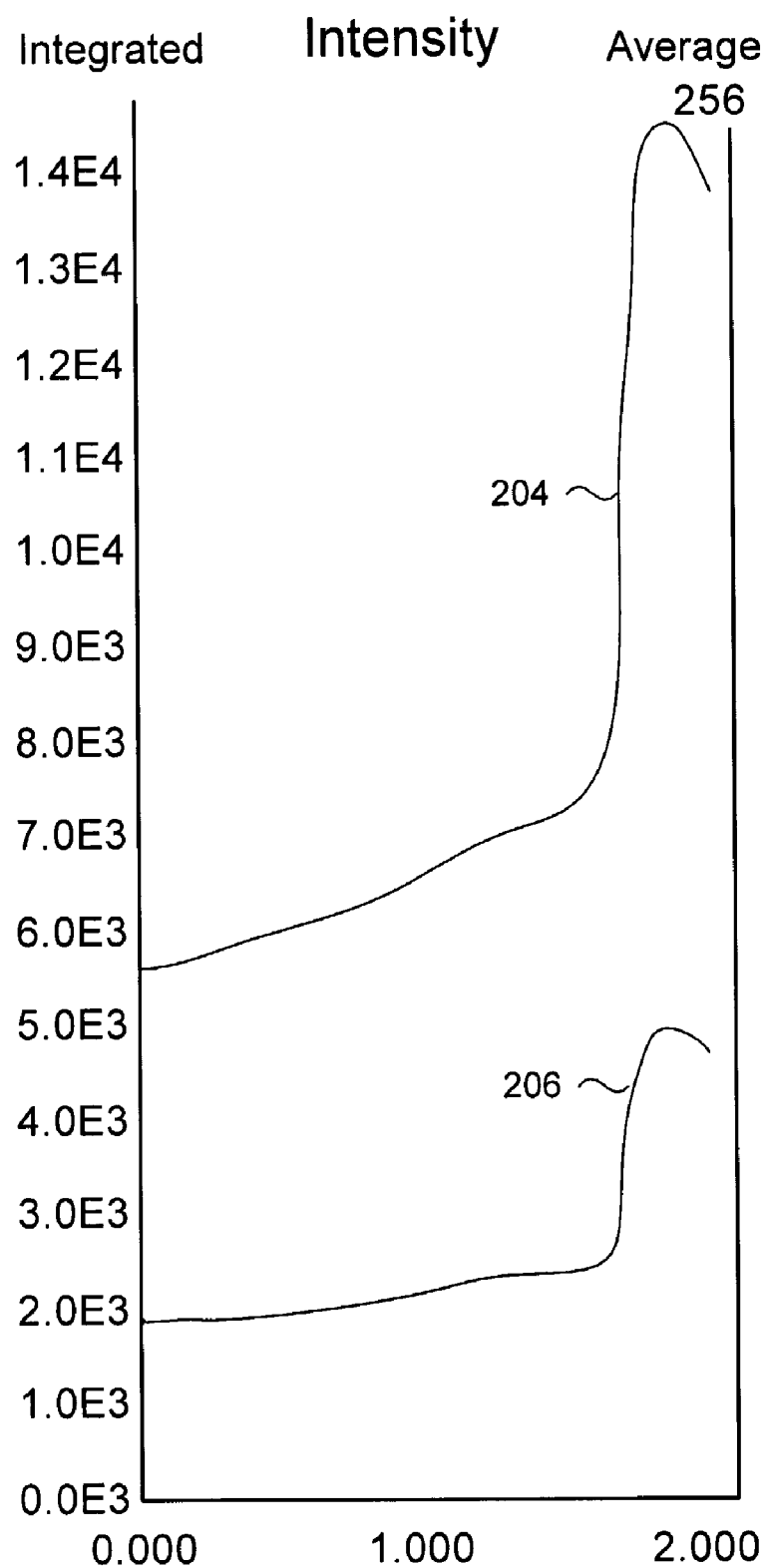
FIG. 6 is a graph of averaged and integrated pixel intensity versus dose/depth generated by the FIB analysis station of FIG. 4 according to an embodiment of the present invention.

FIG. 6 illustrates an example endpoint graph that can be displayed for the user on the monitor of the FIB analysis station 100 according to an embodiment of the invention. The presently shown plot is generated with the same data used by the native FIB system 10 to generate the plot of FIG. 3. The endpoint graph of FIG. 6 includes two plots against respective axes. The left-side vertical axis represents an integrated intensity value while the right-side vertical axis represents an average intensity value. Line 204 is plotted against the integrated intensity value axis and line 206 is plotted against the average intensity value axis. As should be evident to a person of skilled in the art, the plot of FIG. 6 is much more sensitive to endpoint than either the native images or endpoint graph of FIG. 3 provided by FIB system 10. The substantially vertical slope of the integrated intensity plot 204 and the substantially vertical slope of the average intensity plot 206 is indicative of a material transition that can correspond to area 70 of FIG. 3.

Following is a discussion of the functional blocks of the FIB analysis station 100, according to an embodiment of the present invention.

Figure 7:
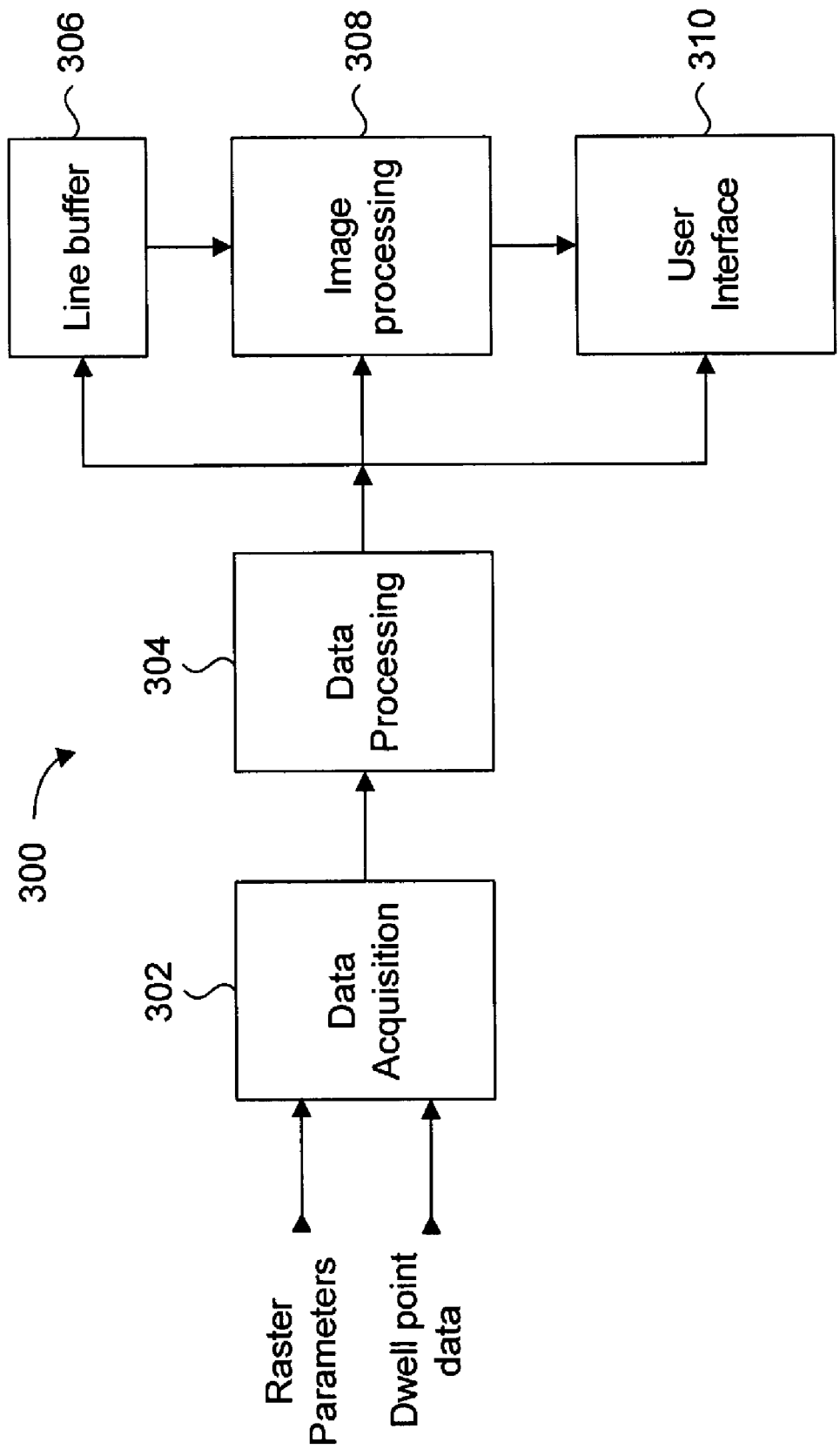
FIG. 7 is a block diagram of a data analysis engine executed by the FIB analysis station shown in FIG. 4, according to an embodiment of the present invention.

FIG. 7 shows the functional blocks of a data analysis engine 300 executed by FIB analysis station 100, according to an embodiment of the present invention. In the presently described embodiment, data analysis engine 300 can be stored as an application program on the hard drive of the computer workstation. Data analysis engine 300 includes a data acquisition block 302 for receiving data from the FIB system 10 via hardware interface 102, a data processing block 304, a line buffer list 306, an image processing block 308, and a display engine 310.

The data acquisition block 302 collects two types of data from FIB system 10. The first can be FIB system parameter data that is sent from the AIX computer to the hardware for maneuvering the ion beam over the sample. This data can include information relating to where the mill box is going to be, the mill box shape and size, dwell time, displacement between pixels, etc. Imaging and milling operations, which can consist of milling, deposition or gas assisted etching, using a number of different raster algorithms, collectively referred to as "mills", can be detected by data acquisition block 302, or provided by a server program residing on the AIX computer of FIB system 10.

The second type of information is the data related to the x-y co-ordinate information of the dwell points and the intensity values of each dwell point. Generally, the data passed by the AIX computer may include information not required by data analysis engine 300. Hence data acquisition block 302 is configured to selectively acquire the data that is deemed necessary to enable the functionality of the data analysis engine 300.

Data processing block 304 receives the two types of data from data acquisition block 302, and executes different functions in response thereto. For example, if raster data is received indicating that a milling operation is to commence, data processing block 304 will send a message ahead to image processing block 308 to inform it of the number of frames/second that will be received so that a 20 frame per second (fps) viewing mode can be obtained. Additional information such as the dimensions of the mill box (to determine the area to be milled), and its location can also be provided so that any received dwell intensity data can be properly organized to generate the proper image.

On the other hand, if intensity data is received, then the image line processing is executed. In the present implementation, the image processing block 308 receives x-y dwell data and intensities, and assembles one horizontal line of data at a time. After each line is assembled, it is added to a buffered list of lines. Each line can include additional information such as the intensities of each dwell point and the mill box the line should correspond to. Those skilled in the art will understand that more than one mill box can be set for a parallel milling operation, and that mill data need not be limited to rectangular boxes.

The data processing block 304 can provide the user interface 310 with information relating to changes in the screen display as dictated by the AIX computer of the FIB system 10. For example, a change in the FOV instruction received by data processing block 304 will cause user interface 310 to update the screen as required. Preferably, any changes on the monitor of FIB system 10 can be reflected on the monitor of the FIB analysis station 100, whether they are user or AIX computer initiated.

Image processing block 308 retrieves a line residing in line buffer 306, and generates a corresponding visual line for insertion into the proper image. Intensity averaging of the line, brightness calculations and any other desired graphical transformations can be executed on the pixels of the line. The image processing block 110 is responsible for executing transformation algorithms upon the image data in order to enhance the image for a particular application. Various image, or graphics processing techniques are well known in the art. A brief description of various the image processing functions that can be implemented follows.

Figure 8B:
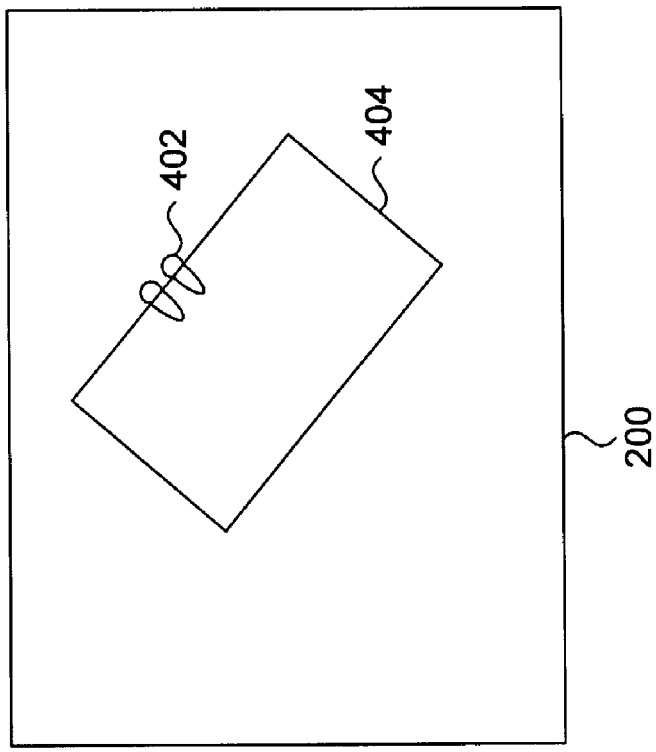
FIG. 8b is an illustration of the originally high eccentricity mill box of FIG. 8a stretched along one axis.
Figure 8A:
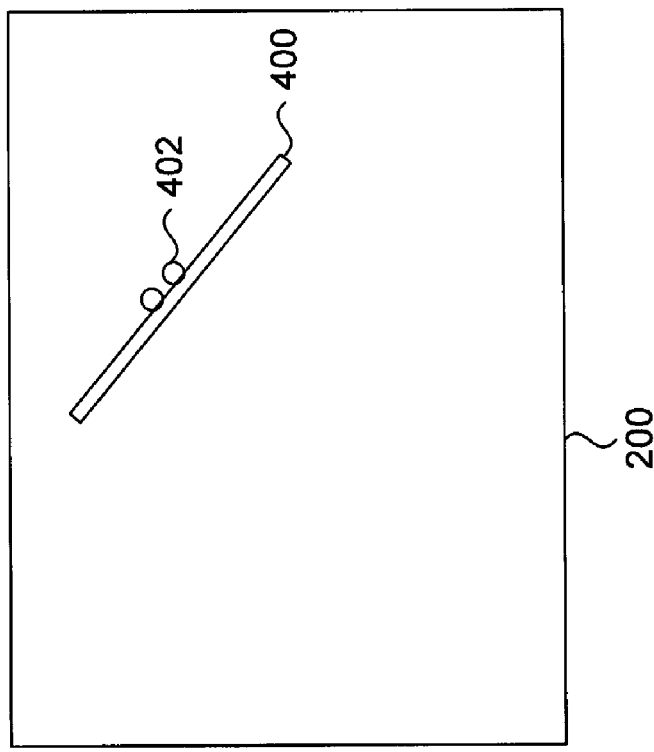
FIG. 8a is an illustration of a high eccentricity mill box with the major axis much longer than the minor axis.

The contrast of the image can be adjusted such that even the slightest contrast change can be detected during milling. Beam focus, stigmation and image contrast level are factors in obtaining the optimum secondary electron image. The image contrast level can be adjusted by referring to a histogram for further optimization. By example, FIG. 8a shows a histogram of a lower contrast image that can be displayed on the monitor of FIB analysis station 100, with intensities ranging from 0 to 164, with the majority of pixels having intensities below 100. FIG. 8b shows the same area, after optimal adjustment of the FIB brightness and contrast to cover the entire dynamic range from 0 to 254, with a reasonable number of pixels at each and every intensity over this range.

The image can be scaled to fit the window with or without "smart" interpolation. Without interpolation, each dwell point results in a distinct rectangle of uniform intensity on the image. If "smart" interpolation is enabled, a smoother image is obtained by interpolating values for the pixels on the display that fall between the exact location of the dwell points in the displayed image, to a maximum number of interpolation steps, after which the image is uniformly scaled. This "smart" interpolation results in a smooth image which still gives the user a perception as to where the actual dwell points fall in the representation.

Alternately, the user can elect to zoom in or magnify an image of either the area being milled or an area simply being imaged. Any predetermined magnification factor, such as by 2, 3, 4 or 10 times for example, can be selected. When an image is to be magnified, the magnified image follows the mouse cursor from view to view. The image can be locked, or anchored, to a specific location if desired.

The displayed image can be stretched in the direction of the minor milling axis. This is useful to expand the pixels perpendicularly to the milling edge, in particular when a high eccentricity box (for example quite wide but not high) is being milled, as often occurs during cross sectioning with the FIB for transmission electron microscopy (TEM) specimen preparation or failure analysis. FIG. 8a shows a high eccentricity ratio imaging box, 400 in viewing area 200 on the monitor of FIB analysis station 100. If the operator desires to precisely mill to the edge of round contact structures 402, determining the exact point at which to stop sectioning in FIG. 8a would be poor as the detail observable from the top on a modern device does not provide sufficient information for precise cross sectioning.

One approach to determining the correct point at which to stop sectioning is to employ a second charged particle beam located off axis from the sectioning beam so as to observe the cross sectioned face in real time, however retrofitting such a column to a single beam instrument is not typically possible and purchasing such a "dual beam" instrument is more expensive than a single beam instrument due to the added complexity of the second column.

Although imaging box 400 may have a height of only several pixels on the display screen of the FIB, there are many more dwell points in the space whose information is not exploited. Thus by anisotropically stretching the imaging box 400 to obtain expanded imaging box 402 as shown in FIG. 8b, more dwell point information can be used to display features that were difficult to see in imaging box 400. As the physics of the milling process lead to a cross sectioned face is not exactly perpendicular to the surface of the feature being cross sectioning, there is always a slight angle to the cross sectioned face, typically a few degrees. If for example, the slope is 2.86°, this results in the cross-sectioned face having a slope of 20:1. Dwell point spacing is relatively small, say 2 nm in the minor axis, and the display of the data from the milling box is anisotropically stretched by a factor of 20 in the display of the minor axis of the mill box as in the present example. The resultant stretched image displayed will compensate for the 20:1 slope of the cross sectioned face leading to a display with nearly 1:1 aspect ratio where portions of the contacts 402 within the edge of imaging box 404 are correspondingly stretched, achieving an effect not dissimilar to what is obtained by examining the cross sectioned face with a second, off axis beam. Therefore, the operator can more precisely position the edge of imaging box 404 and determine the optimal point and location to stop sectioning. In practice, the operator would position the imaging box 402 on FIB system 10, with the expanded imaging box 402 on the monitor of FIB analysis station 100 being correspondingly positioned, or make very fine adjustments to the position of the box during milling by examining the anisotropically stretched display of the milling image.

Conversely, the displayed image can be shrunk, or scaled down to a fraction of its full size by stretching using a factor less than 1. This can be useful to reduce pixelation when interpolation is turned off and when boxes with few dwell points are being milled, so as to let the human eye more readily differentiate variations in the information displayed.

As previously mentioned, image processing block 308 can execute calculations for displaying imaging or milling data. These include a live, TV, integrated, averaged, snapshot and differential modes of imaging. A brief discussion of each of these imaging modes follows.

The live imaging mode displays individual frames of data on a fixed range corresponding to the number of bits of intensity data provided by the detector, typically an eight bit, 0-255 range.

The TV mode displays averaged frames of data, where the number of frames that are averaged is calculated such that the averaged frame rate is 20 fps (the necessary fps to produce a smooth "TV"-like image). This number is automatically calculated from the rastering information and cannot be changed. It usually provides the best imaging as a compromise providing good signal to noise ratio yet retaining a good responsiveness to rapid changes in the image data.

The integrated mode displays integrated frames of data. At any given time, the displayed image corresponds to the sum of the previous N frames, where N is selectable by the user.

The averaged mode is similar to the integrated mode, but a histogram function can be used to scale its limits to a 0-255 scale, or to whatever scale is appropriate based on the full range of the detector providing the signal under examination, thereby limiting the precision in selecting channels, but displaying it on the same range as the Live or TV modes.

The snapshot mode displays integrated frames of data in quarter second intervals. The data displayed in the endpoint intensity graph is obtained from these images. They are only updated every quarter second, independently of the rastering time. Because this is not a rolling average, each image can be the sum of more than 32 frames. Histogram limits are scaled down to the appropriate range.

The differential mode displays a composite image based on the snapshot images acquired as ¼ s integrated images. The differential image can be calculated as the difference between the most recent snapshot and the previous 4 snapshots weighted by factors of 0.50, 0.25, 0.15 and 0.10 respectively for the most recent to the most ancient snapshot images. Those skilled in the art will realize that these ratios provide a measure of both persistence in a feature being examined coupled with a decay time for this persistence to fade, however other ratios can be employed that will also create the impression of persistence with decay, mimicking a behavior not unlike the behavior of the phosphor elements of a crt radar display. Although 4 snapshots are used, any number of snapshots and corresponding weightings can be used.

Using this scheme, when all snapshot data is normalized to 8 bit intensities, the calculated difference data can extend from −255 to +255, so it is again divided by 2 and offset by 127 to yield a 0-255 range on which any normal palette can be applied for display purposes. The weighing of components of previous images produces a persistence that extends over approximately 1 s, similar to a phosphor persistence effect on a CRT radar display. This reduces jitter in the imaging and permits the user to better perceive changes as they occur more gradually than if a simple difference between only two snapshots was performed. A region of the milling image that becomes brighter appears bright in the differential image and a region of the milling image that becomes darker appears dark in the differential image. In the absence of change, the data is centered around channel 127 on the 0-255 range. This view is particularly good for determining regions of a mill box that have recently appeared or disappeared.

Figure 9:
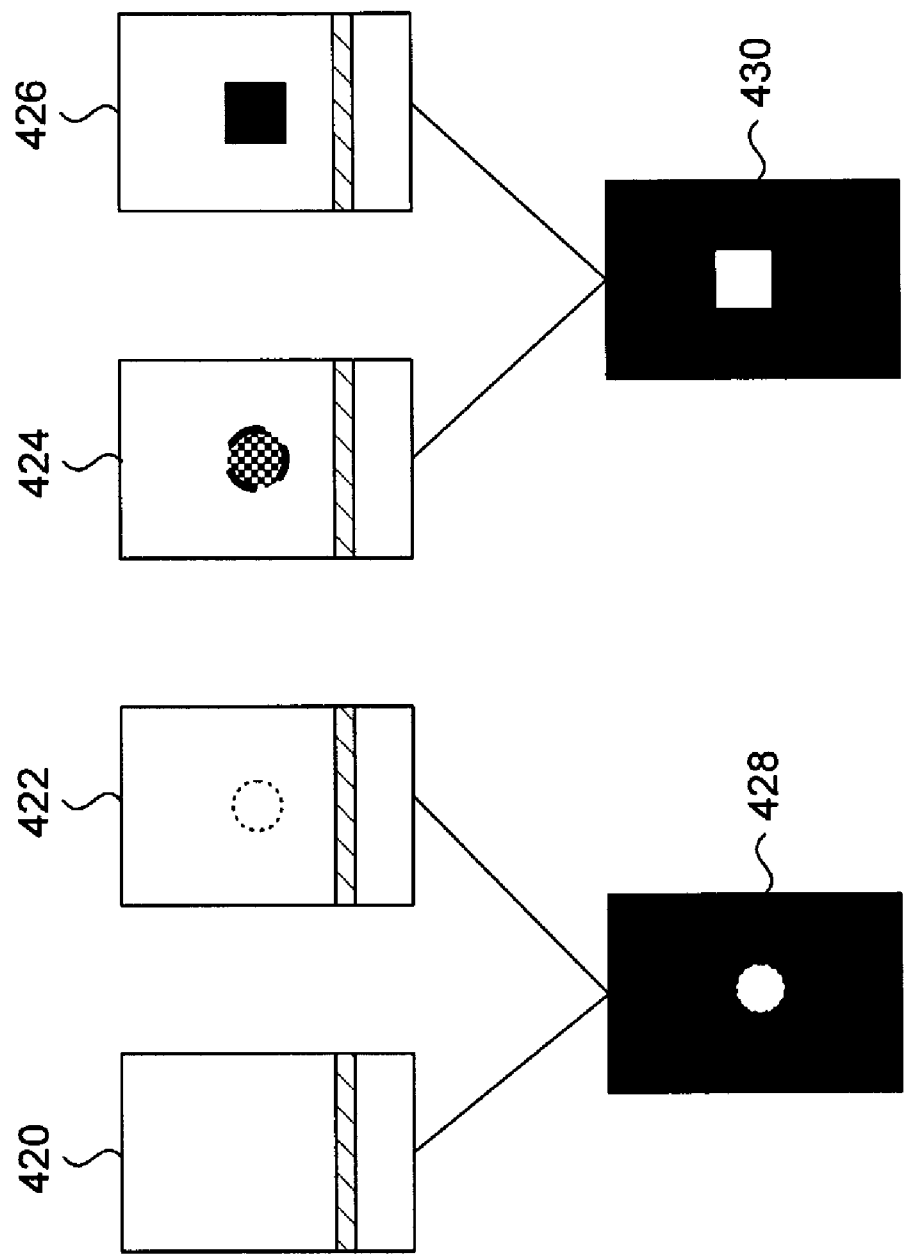
FIG. 9 illustrates a differential imaging mode, according to an embodiment of the present invention.

FIG. 9 illustrates a sequence of snapshot images and the corresponding differential images resulting therefrom. Snapshot images 420, 422, 424 and 426 of a milled area taken at quarter second intervals (from left to right) illustrates the progressive appearance of a square and a metal line structure extending horizontally at the bottom portion of each snapshot. The backgrounds of each snapshot is a light grey colour, and the milled area initially appears as a light circle in image 422. As milling continues, the circle may darken as shown in image 424, until a full dark box mill appears image 426. In the differential mode of operation by example, image 420 (and the previous preselected number of images) is subtracted from image 422 to generate differential image 428, while image 424 is subtracted from image 426 to generate differential image 430. The grey backgrounds have not changed, resulting in a black background, but the dark circle appearing in image 422 will now appear as a bright circle in differential image 428. Similarly, since the only change between images 424 and 426 is the square box, differential image 430 will only show a bright square box. Note that because the horizontal metal line has not changed in any of the snapshots, it will not appear in the differential images. While the presently described embodiment subtracts four previous images from an image of interest, any number can be selected, as can the weightings applied to each previous image.

According to an embodiment of the invention, a user selectable colour palette can be applied to the differential images to represent the type of change occurring. For example, the black colour can indicate that no change has occurred. Hence the user can quickly see any changes occurring during the mill. Further discussion of the selectable colour palette is discussed later.

User interface 310 is responsible for displaying the images and plotting the endpoint graphs on the monitor of FIB analysis station 100. Furthermore, the monitor allows the user to select various features and functions, or to switch views The user interface 310 is generally responsible for the visual layout/presentation of the graphical data and image data for display on the monitor of the FIB analysis station 100. This graphical data can include an endpoint graph such as the one shown in FIG. 6, images, thumbnails, FIB parameter information, and user selectable features for controlling the type of information for display. For example, the user can select the differential imaging mode if desired, or multiple panes for viewing the image in more than one mode, or multiple panes for viewing multiple images from different mill boxes, each having its own mode and color palette applied.

As previously discussed, the user can select a colour palette to specify what colors are assigned to the measured intensities. A default greyscale palette provides a linear scale of greys between black for no intensity and white for full intensity. Several other palettes can be used for false colour rendering of the milling images, which can make small variations in the intensity more noticeable. Some palettes of particular interest including a Thermal palette ranging from black to white through the range of reds and yellows, and a Red-Green-Cyan palette where low signal is a deep red, medium signal is a solid green and high signal is a bright cyan. The order of the palette can be inverted, such that white can be used for no intensity and black for full intensity. The user interface 310 can assign the user selected colour palette to the intensities and correspondingly display the intensities with the selected colour palette on the monitor.

As the human eye can only distinguish somewhere between 64 and 256 discrete grey levels, most palettes are limited to 256 entries, however it can be advantageous to display more than 256 different levels. In this case a larger palette containing different colors, either continuously varying in tone as is the case of the thermal palette or as a selection of discrete colors where the difference between one palette entry and the next or one region of the palette entried and an adjacent region are substantial. Such false color palettes have proven effective in increasing the perception of change in the milling images that are displayed when compared to the greyscale palettes of the current art. False color palettes are also advantageous even if they are limited to 256 or fewer entries.

Gamma correction can be applied to the selected palette. Gamma correction is used to induce a non-linear relationship between the actual signal intensity and the way it is displayed, which can make the image more sensitive to small changes at the low or high intensity end of the signal range. A gamma of 0.0 results in a linear relationship. A positive γ results in low intensities appearing brighter more rapidly with the response at high intensities remaining relatively unchanged. A negative γ results in high intensities appearing brighter more rapidly with low intensities being relatively unchanged.

A unique feature of user interface 310 is the generation of the sensitive endpoint graph, such as the one shown in FIG. 6. The endpoint graph shown in FIG. 6 is plotted in real time on the monitor of the FIB analysis station 100, with a scale that can dynamically adjust itself according to the intensity values being received from the image processing block. In the present embodiment, the user interface 310 prompts the image processing block 308 every quarter second for an intensity value, be it an averaged or integrated value of the last frame. A quarter second is merely a preferred time interval, and any predetermined interval can be used without departing from the scope of the invention. It is noted that a brightness value can be calculated at the end of a frame, or after a predetermined period of time if the raster is slow. For example, if a raster frame requires a relatively long time to complete, then the image processing block 308 can use the data collected after a predetermined time the rastering of the frame began to generate the brightness value. Accordingly, a frame can be defined as including the dwell point intensity data collected for a specific period of time during which the FIB is rastering the sample. This specific period of time can correspond to the time required to raster one full frame.

In particular, averaged image data with 0 to 255 intensity values and integrated image data with thousands of counts per dwell point, are used by user interface 310 to plot the endpoint graph in real time. The endpoint graph can be dynamically auto-scaled by resealing the "y" axis from the minimum to the maximum values of the data displayed on the "x" axis. A full scale operation re-plots the integrated data from the minimum to maximum "y" axis values for all data points in the present mill, regardless of whether they are currently displayed, while a rescale operation performs the same re-plot, but only for the range of "y" axis values presently displayed. In all cases, if the integrated intensity graph were to exceed the upper or lower "y" axis limits, the graph will rescale. One can increase the ease of perception determining when changes in the intensity values are occurring by choosing to rescale the "y" axis data when the variation in the "y" axis data is small over the range of the "x" axis displayed on the graph. It is advantageous if this action can be performed with a single user event such as a mouse click. After this resealing event, then small changes in the "y" axis data become readily apparent, which has proven advantageous in determining endpoint conditions in comparison to the current art. Those of skill in the art will understand that graphical re-scaling is a straightforward mathematical function.

Furthermore, in contrast to the native FIB system 10, the endpoint graph provided by user interface 310 has a sensitivity that is independent of the field of view setting on the FIB system 10.

Using the data from image processing block 308, user interface 310 can generate a cross-sectional image of the milled area of the sample in real-time, to supplement the endpoint graph and planar images that are provided. Further discussion of this feature will be discussed later with reference to FIG. 10

Accordingly, the previously described imaging and endpoint graphs generated by FIB analysis station 100 are advantageously used for endpointing operations of FIB systems. This is primarily due to the fact that all the dwell point intensity information is used for generating the images and the highly sensitive endpoint graphs that plot averaged and integrated brightness values of the image frames. With the enhanced images and endpoint graphs generated by the FIB analysis station 100 that are clearly superior to the native FIB system 10 produced images and endpoint graphs, a FIB operator will have improved confidence in determining proper endpointing. Therefore, FIB assisted microsurgery using the embodiments of the present invention will result in a higher rate of success.

As previously discussed, reliance upon an operator's memory to conduct post endpointing analysis is neither practical nor dependable. What is required is a comprehensive job logging system that records all images acquired, all endpoint graphs produced and a concise visual record of all milling operations. This job logging system can then provide all the information available from the microsurgery that has been performed for later review. In this manner, it is possible to greatly increase the confidence that a FIB circuit edit has been performed correctly. For example, the test system may produce a result that can be analyzed to determine that the unexpected result could arise from a microsurgery join inadvertently shorting to a neighboring signal line. This short may not have been observed by the operator at the time, but with a comprehensive job logging system that enabled later review, the short can likely be identified, thus proving that the erroneous result is due to a FIB error. This ability to review a job at a later date is advantageous as it reduces the necessity to perform time consuming destructive failure analysis on the device that has undergone surgery to look for possible shorts, etc. Additionally, once this system is available to a microsurgery operator skilled in the art, it is possible to review a job that appears "flawless" and comment with a high degree of certainty that the microsurgery has been a success and that the problem is likely with the proposed design change.

Since the data analysis engine 300 is preferably executed on a computer workstation, the history of the mill, endpoint graphs and all acquired images can be recorded on the hard disk drive for future reference and playback for training or a "post mortem" of the mill. The data can be transmitted over a network for playback on any computer system. Virtually any type of information collected or generated by data analysis engine 300 can be stored. For example, each image pass is recorded, in sequence, as well as each milling operation (milling, gas assisted etching, deposition), with the full set of thumbnails generated for the mill and the endpoint graph signals (both intensity and stage current, if available). The aperture setting, beam currents and cumulative dose throughout the mill, x and y spacings as well as dwell times, box size, position and raster style (raster, serpentine, polygon, etc.), stage position, along with other instrument parameters, etc. can be recorded. A unique screen interface can be presented on the monitor of FIB analysis station 100 for the user to review a recorded mill. Alternately, this screen can be used to track a mill in real-time as the mill information is being recorded. It should be noted that in one embodiment, this information is also encapsulated for transmission over a network to another site where it can be viewed remotely.

Figure 10:
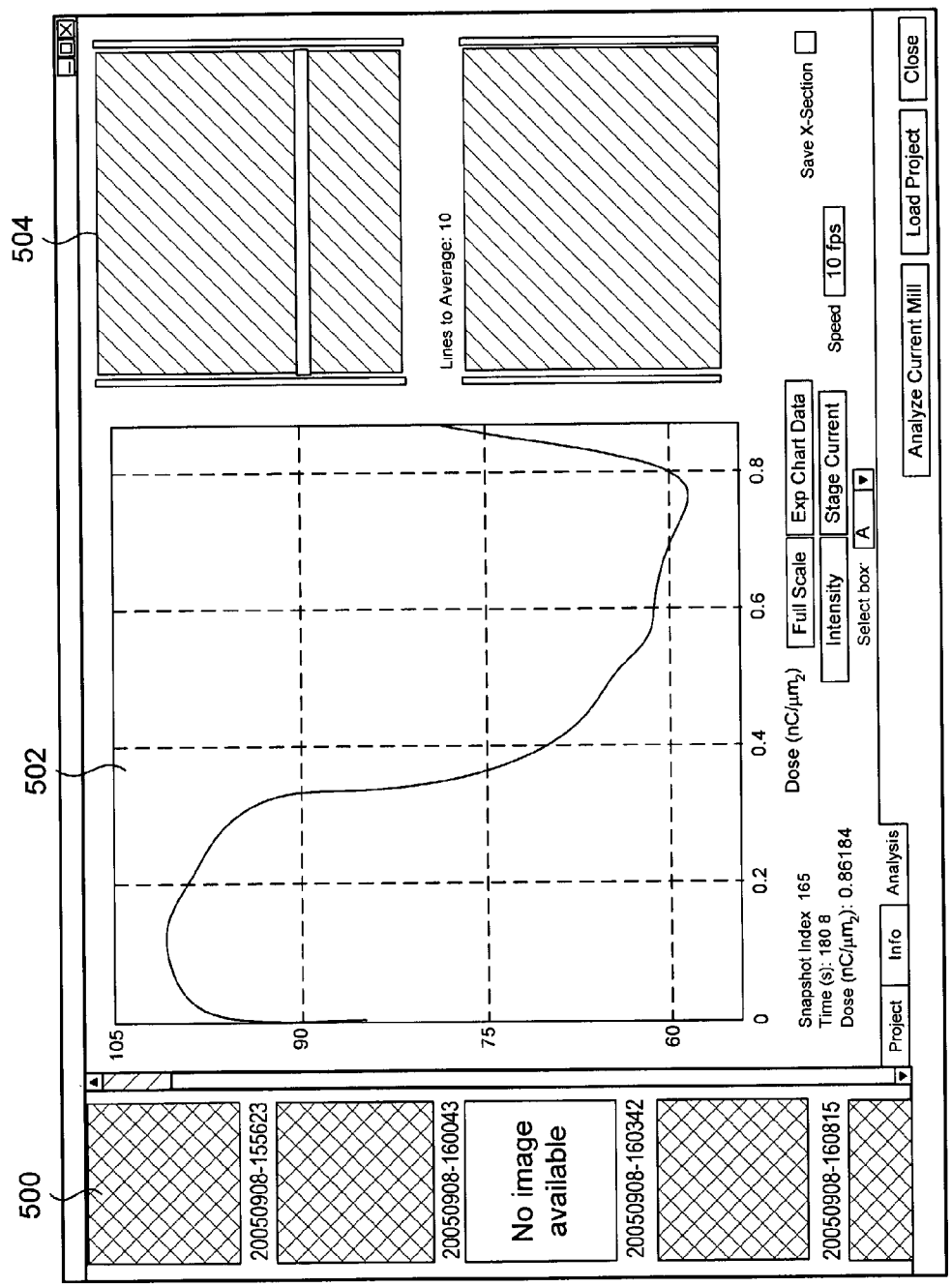
FIG. 10 depicts a project review user interface screen, according to an embodiment of the present invention.

FIG. 10 illustrates an example user interface screen for reviewing a project. The user interface screen shows a mill chronology list 500 for displaying thumbnail images of the mill in chronological order, an endpoint graph 502 and a cross-section panel 504. The endpoint graph 502 is interactive, meaning that clicking at any point on the graph brings up the associated thumbnail and an indication in the cross-section panel 504 of the corresponding depth. This user enhancement feature can easily be enabled by cross-linking the plotted data points on the endpoint graph 502 to the thumbnail images, and to the horizontal lines of the cross-section image. Hence the user can click on a particular thumbnail to view its corresponding position on the endpoint graph and in the cross-section image. Alternately, the user can select a particular point on the endpoint graph to view the corresponding thumbnail image and depth indication on the cross-section image. Of course, selecting a particular depth on the cross-section image will bring up the corresponding thumbnail and point on the endpoint graph. The mill can be reviewed ("played") forward or backward from any point on the endpoint graph 502.

Figure 11:
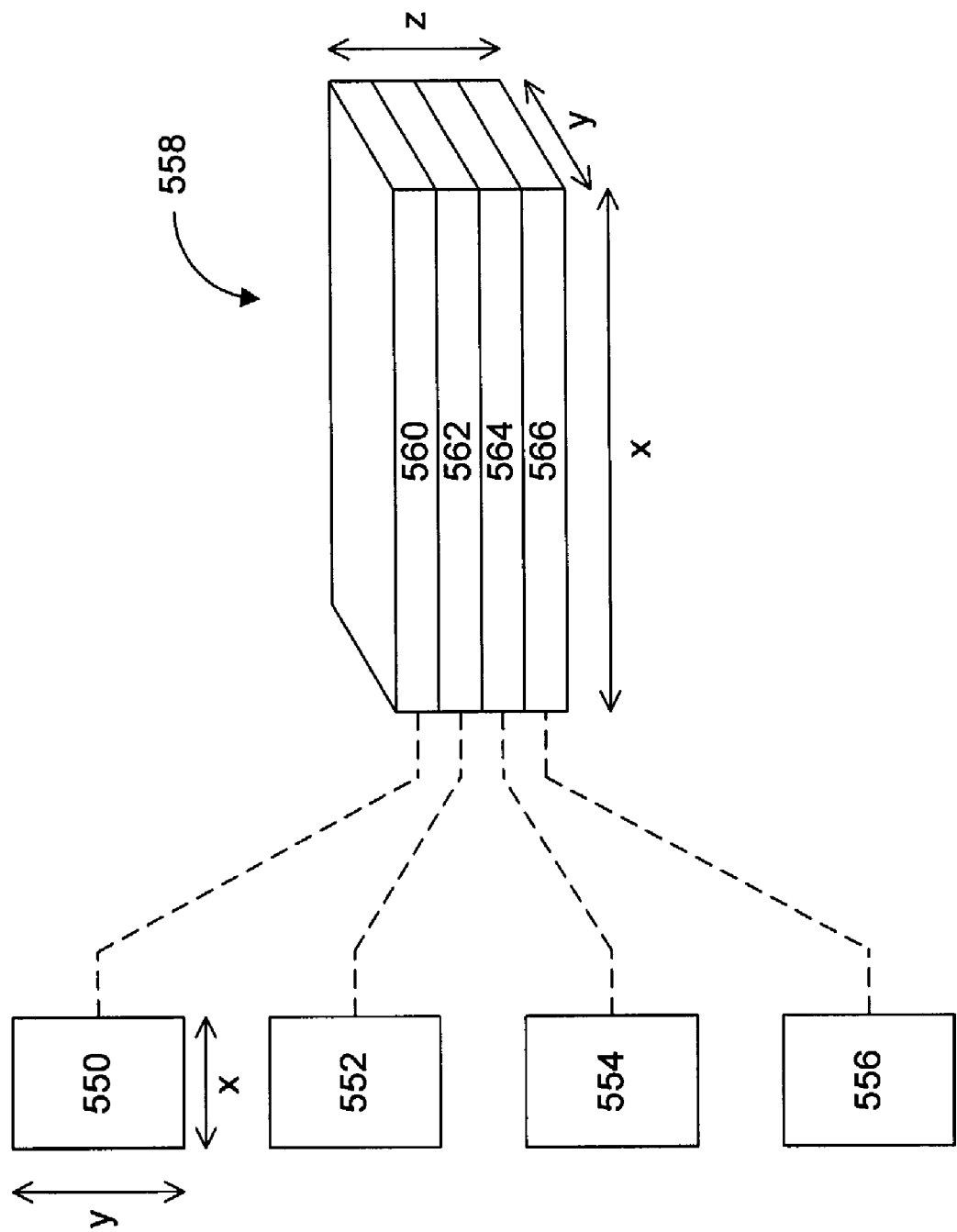
FIG. 11 is an illustration of a cross-section image generated from planar image data.

The cross section image in panel 504 is generated by assembling sequential images as shown in FIG. 11. FIG. 11 graphically illustrates the correlation between images and the constructed cross-section image. The top-most thumbnail image 550 is the first to be generated in time during a mill, followed sequentially by thumbnail images 552, 554 and 556. A cross-section stack 558 can be constructed as the thumbnail images are generated. A line starting at the top portion of cross section view 558 is added every time a thumbnail is produced, and corresponds typically to a vertical or horizontal slice of the thumbnail, although a slice at any angle can be constructed. As shown in FIG. 11, cross-section lines 560, 562, 564 and 566 correspond respectively to the thumbnails 550, 552, 554 and 556.

As such, the horizontal axis (labeled x-axis) of the cross-section corresponds to space and the vertical axis (labeled z-axis) corresponds to time (or equivalently dose and is thus somewhat related to depth). The user can also select whether the cross-section is created from horizontal, vertical or arbitrary slices of the thumbnail images. Line and width parameters can be user selectable to indicate which area of the thumbnail is used to create the cross-section. For example, if the thumbnails are 200×200, setting the line parameter to be 100 means the cross-section will be produced from the middle of the thumbnail image. The width parameter indicates how many lines of the thumbnail, centered about the cross-section line will be averaged to produce each cross-section line. Intensities can be integrated or averaged along the vector perpendicular to the cross section line whose length is specified by the width parameter. Note also that the user can select the location of the cross-sectioned line using graphical user interface tools rather than specifying the "Line" parameter.

A significant advantage of the cross-section image generation illustrated above is to assist in device reconstruction. More specifically, a site on the chip where a failure is expected can be milled to remove a cuboid volume (x by y by z), and then analyzed using the cross-section image generated above to determine if there is a lack of electrical contact between two elements. Since the mill operation is stored, the specific region that failed can be re-built through metal deposition in the cuboid volume. In particular, the stored cross-section image can provide an indication of the relative spatial position of the two elements with respect to each other. The chip can then be electrically tested to see if proper functionality is obtained.

In addition or alternate to recording the thumbnails, images and endpoint graph of the mill, the data processing block 304 can have the generated lines saved as they are fed to the line buffer 306. This saved data can be run and re-run at a later time to allow the operator to experimentally preset optimal image settings for subsequent similar mills. This feature also functions as a training tool that can be executed without FIB system 10, since the data can be loaded from mass media to a standalone computer or laptop running the data analysis engine 300.

Figure 12:
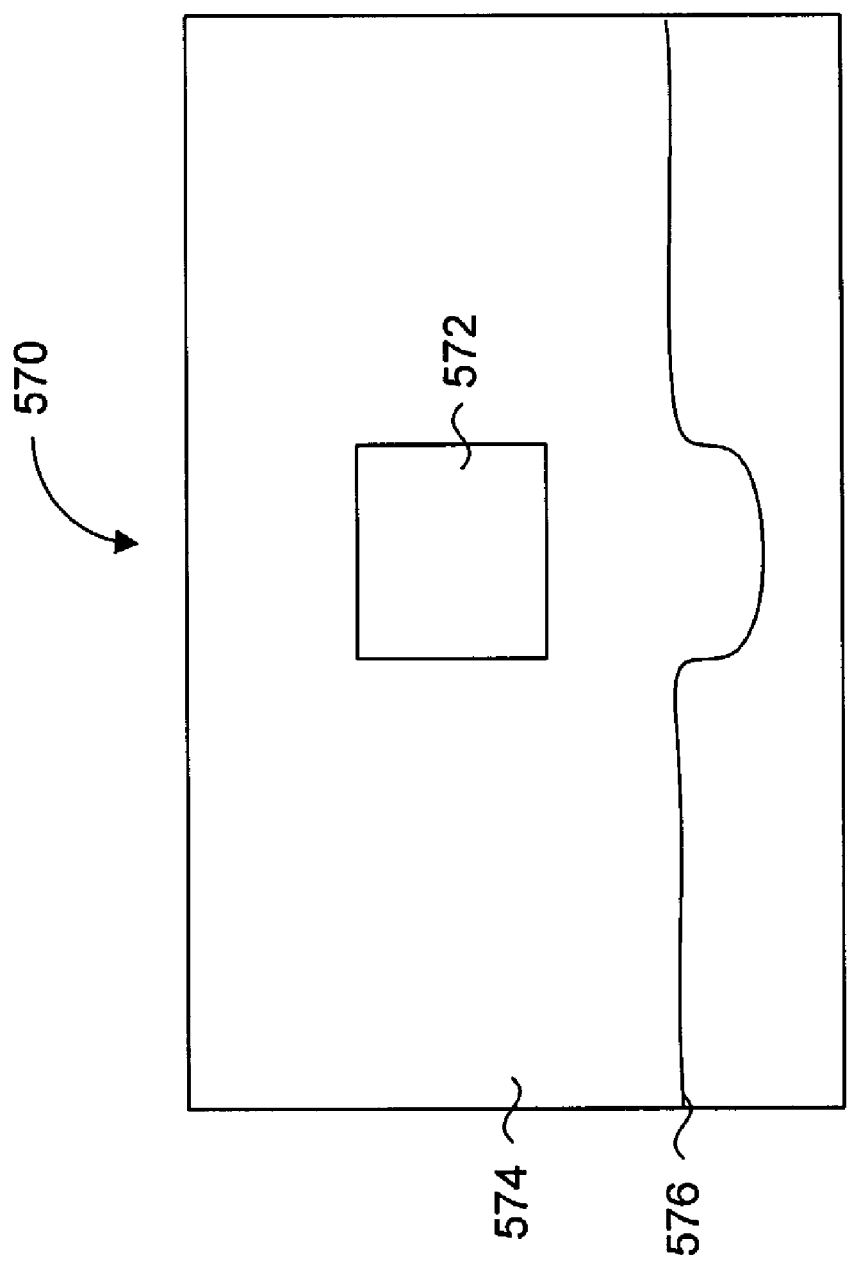
FIG. 12 is an illustration of a generated cross-section image affected by varying milling rates.

A physical fact of FIB milling is that different materials may mill at different rates because the milling rate often varies as the material being milled varies in composition or crystallographic nature. Hence, if the mill encounters a material with a slower milling rate than the surrounding material, then the data for the material beneath the structure, such as the substrate, will be offset and appear later in time relative to the surrounding material. FIG. 12 illustrates a cross section view 570 showing a metal structure 572 within a uniform oxide dielectric material 574, and a generated substrate delineation line 576. Due to the slower milling rate through metal structure 572, by the time the mill underneath metal structure 572 has truly reached the substrate, it will be at a time after the mill surrounding the metal structure 572 has reached the substrate. Therefore, substrate delineation line 576 underneath metal structure 572 will have a "U"-shaped dip.

Since the "U"-shaped dip is known to be occurring at an inaccurate "depth" or dose relative to the remaining portions of the line, corrective algorithms can be implemented. For example, a simple algorithm would be to re-normalize the data points of the "U"-shaped dip from the surface of the sample to the proper reference point, that being the remaining portions of the substrate delineation line. More specifically, one means of reconstructing a more accurate cross-section is to project the measured variation of a known surface (such as the interface between the interconnect layers and their dielectrics on an integrated circuit and the silicon substrate on which the IC is built) and mathematically correct for deviations between the known position of this surface and the observed positions, then applying this correction to the layers above to obtain a better fit. An example of a more complex algorithm is to analyze the signal intensity during the mill operation and detect those areas that are milling slowly. Hence corrective calibration can be applied dynamically to compensate for the differences in milling rate.

Other techniques can be used to detect the reduced rate of milling, such as by detecting the combined electron and ion signal using a positive biased detector and a negatively biased detector in order to classify the material being sputtered and apply a calculated or predetermined sputter rate. Once the sputter rate is determined, calculations can be made to correct the image.

For example, one can observe the secondary electron and ion signals (perhaps filtering either or both signals for more information, i.e. examining different energy ranges of the secondarily emitted electrons such as backscattered electrons, which are lumped into the term "secondary particle" for the purposes of this document, and/or mass filtering the secondary ions) and develop a formula for estimating the relative sputter rate of the different materials based on these signals, and using this to calibrate the depth of material removed in each milling pass. For example, a formula based on observing the total secondary ion yield and the total secondary electron yield at each point (these signals being collected either sequentially by varying the detector characteristics on alternate primary beam scans or scan lines/pixels, or simultaneously using multiple detectors) is able to remove some of the ambiguity arising from crystalline variations within a given material and also aid in determining the material from a list of known or expected materials (the basic expectation of which materials are present in an integrated circuit being known). From this data, by classifying which material is at which position and normalizing for variations in sputter rate that arise from variations in the crystalline character of the material, it is possible to apply previously determined sputter rates to the three dimensional data so as to better calibrate and correct for variations observed and therefore more accurately represent the true position of features in the displayed data, without needing to rely on an extrapolation from a known surface.

As shown in the previously described embodiments of the invention, having all the dwell point information available to the data analysis engine 300 will enhance FIB endpointing operations, especially since standard graphical and mathematical calculations can be performed to enhance images and endpoint graph sensitivity.

The dwell point information can be used to overcome known problems, or difficulties, for specific types of FIB endpointing operations.

Figure 13:
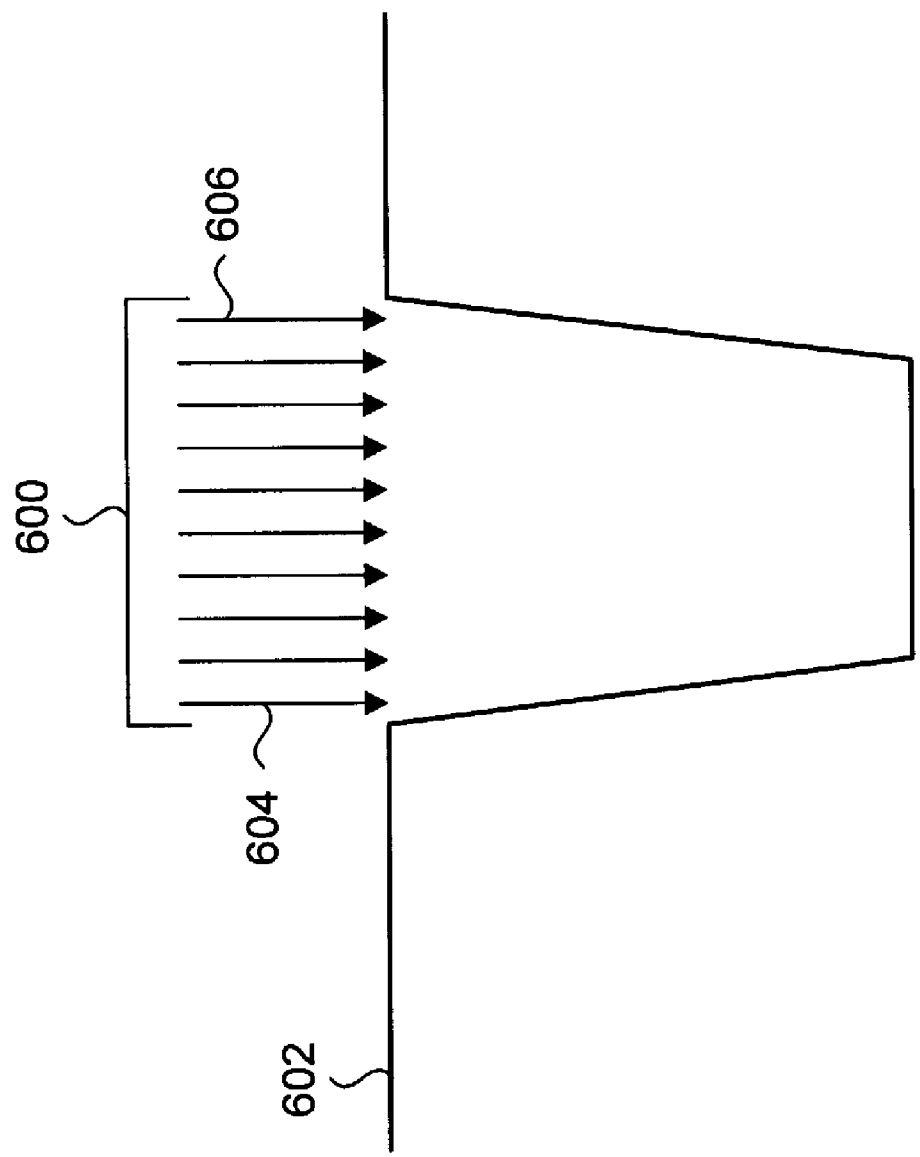
FIG. 13 is a cross-section illustration of a milled sample.

For example, the Mach banding effect is a well known phenomenon of the human eye's perception where the side of a higher intensity (brighter appearing) stripe near the lower intensity (darker appearing) stripe appears brighter than elsewhere across the stripe even though physically the stripes are uniform across their full extent. Likewise, darker stripes that are uniform across their full extent appear darker on the side near the brighter stripes. Such sharp bright and dark transitions commonly occur during FIB milling operations. FIG. 13 is a cross-sectional image of a sample being milled to illustrate this effect. Another effect arises from the fact that beams of charged particles 600 rastering the material 602 will often mill a trench structure with sloping sidewalls. Unfortunately, the angle of the resulting sidewall causes a relatively large signal intensity from peripheral beams 604 and 606 due to the enhanced yield of secondary particles that is known to occur when the surface being hit by the milling beam approaches closer to being parallel to the incident beam rather than perpendicular to it. When imaged, the large signal intensity from these dwell points may falsely indicate to the operator the presence of lines encountered during the mill, or if nothing else the high signal from this region can swamp the signal from the central region of the mill where it is anticipated that the signal most of interest will arise. Because the resulting image is dominated by the bright edges, contrast and brightness adjustments will only marginally improve the image.

According to an embodiment of the invention, the data analysis engine 300 can selectively ignore the data from any number of peripheral dwell points, i.e. peripheral beams 604 and 606, and use only the data from the remaining dwell points. Since all parameters of the raster environment are known, such as the location and size of the mill box, the image processing block 308 can selectively ignore the dwell point data proximate to the edges of the mill box. Any number of dwell points near the mill box perimeter can be ignored. Therefore, the image contrast and brightness levels can be adjusted over a wider range since they are based on the most sensitive dwell point areas. Even though fewer counts are available for the endpoint graph, sensitivity is actually increased.

Figure 14A:
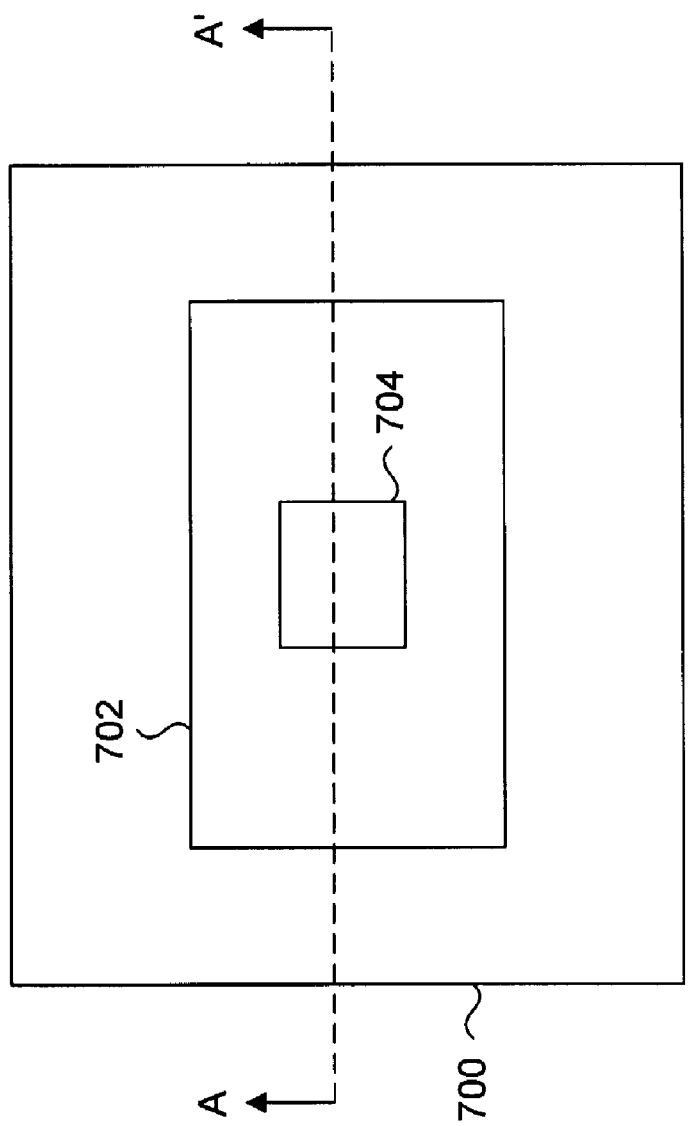
FIG. 14a is a planar view of a chip with nested milling boxes.
Figure 14B:
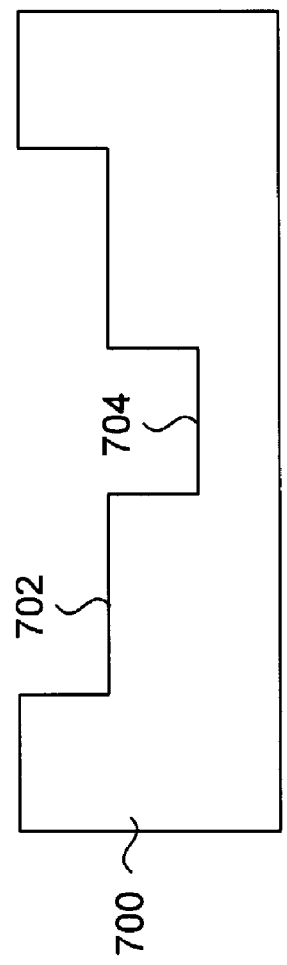
FIG. 14b is a cross-section view of the chip shown in FIG. 14a along line A-A'.

The advent of "flip-chip" mounting of semiconductor chips in a package presents certain challenges. FIB microsurgery must be done from the backside of the device, and an initial exploratory mill is typically performed over a large area of the device to determine the distance, or milling time, between the substrate and the active components of the device. FIG. 14a is a planar view of the substrate of a chip 700 and nested mill boxes 702 and 704. Since mill box 704 is within box 702, the area within box 704 will received double the dose as the area within box 702 and mill at a higher rate. FIG. 14b is a cross-section view along line A-A' in FIG. 14a. The goal is to mill until a known structure is encountered through mill box 704, thus requiring accurate endpointing to stop the process. However, any signal received from box 704 is effectively reduced relative to the signal from the area of mill box 702. For example, if the area of mill box 704 is A, a brightness level representing the presence of the desired structure only represents 10% of the aggregate signal if the area of mill box 702 is 10 A. Therefore, a small change to the area of mill box 704 will be even less perceptible to the human eye since the signal from mill box 702 behaves as noise that washes out the signal from mill box 704.

Since the dwell point information of both mill boxes are known to the data analysis engine 300, the user can selectively decide to view only the endpoint and image data for the mill box of interest, mill box 704. Hence the dwell point information from mill box 702 is ignored for the purposes of endpointing with mill box 704. Alternately, the system can chose to process and display only the signal from a selected region of interest on the device, which could include, for example, all of mill box 704 and the portion of mill box 702 that overlaps with mill box 704. Note that after this processing, subsequent processing such as the discarding or masking of mill points near the perimeter of the analyzed region can also be applied. Similarly, the user may chose to display the information from the same analyzed region in multiple ways at the same time, using, for example, multiple image palettes and or multiple conditions such as varying the integration parameters, choosing to view TV, Snapshot and Differential modes of imaging at the same time, etc. This ability to compare and contrast the same data under different analysis conditions has proven to be very effective in successfully determining endpoint conditions in comparison to the present art.

When placing one or more mill boxes on the screen, an anchor point or reference marker is usually added to the screen to ensure proper placement or orientation of the mill boxes. For example, the mill boxes can be placed at a specific position relative to a structure visible on the sample. However, drift may cause the mill boxes to shift slightly, and it is unlikely that the original position of the mill boxes can be obtained. In the native FIB system 10, a dummy mill box would be used to outline the visible structure. However, the sample may be milled within the dummy mill box, albeit at a minimum dose. According to another embodiment of the present invention, the user can draw a true reference marker on the monitor of the FIB analysis station 100 that is locked to the mill boxes of FIB system 10 (which are re-drawn on the monitor of FIB analysis station 100). If drift does occur, the operator can shift reference marker back to its original intended position by shifting the mill boxes via the controls of FIB system 10.

While the previously described embodiments of the invention use dwell point intensity data for generating the endpointing graph and images, other data that can be cross-referenced to the dwell point location on the sample can be used. For example, a measurement of absorbed current, ultrasonic acoustic signal, or light emission from the sample can be obtained for each dwell point and used alone or in conjunction with the intensity values to further enhance the endpoint graph or image data for the operator. These other types of data can also have corresponding intensity values for each dwell point of the beam.

The previously described embodiments of the invention are not limited to FIB systems, and the aforementioned techniques can be applied to any charged particle beam (CPB) microscope that is used to modify the material that is being examined. Examples of such charged particle beam systems include a scanning electron microscope (SEM) with a gas delivery system providing a reactive gas, for example. Those of skill in the art will understand that adapting the aforementioned embodiments can be easily adapted to function a with a particular charged particle beam system.

The above-described embodiments of the present invention are intended to be examples only. Alterations, modifications and variations may be effected to the particular embodiments by those of skill in the art without departing from the scope of the invention, which is defined solely by the claims appended hereto.

The invention claimed is:

1. A method for enhancing endpointing determination in a charged particle beam system operation involving material modification, comprising:
   a) receiving dwell point information from each frame generated by the CPB system, the information including dwell point intensity values;
   b) processing the dwell point intensity values of a first region of interest of a first number of frames to derive raster data, and when the first region of interest is defined, mapping the raster data to an image palette and displaying the resultant raster image;
   c) plotting a summation of the dwell point intensity values of a second region of interest of a second number of frames on an endpoint graph versus charged particle dose or rastering time, when the second region of interest is defined.

2. The method of claim 1, wherein the raster data is mapped and displayed after one of a predetermined time interval has elapsed, a predetermined dose increment is received or a predetermined number of frames has elapsed.

3. The method of claim 1, wherein the summed dwell point intensity values are plotted after one of a predetermined time interval has elapsed, a predetermined dose increment is received or a predetermined number of frames has elapsed.

4. The method of claim 1, wherein the first number is automatically calculated to obtain raster images having an appearance of real-time responsiveness to changes and improved signal to noise ratio over a live raster image.

5. The method of claim 1, wherein each raster data is processed by summing the dwell point intensity values of the first number of frames, resealing the raster data from a selected minimum value to a selected maximum value over a predetermined scale, where values in the raster data less than or equal to the selected minimal value become a new minimum value and values in the raster data greater than or equal to the selected maximum value become a new maximum value, and applying another image palette mapping that ranges from the new minimum value to the new maximum value and displaying the resultant scaled raster image.

6. The method of claim 1, wherein the raster data mapped to the image palette remains unchanged until one of a predetermined time interval has elasped, a predetermined dose increment is received or a predetermined number of frames has elapsed.

7. The method of claim 1, further including a step of generating a differential display image from a difference between current raster data and a predetermined number of previous raster data.

8. The method of claim 7, wherein each of the predetermined number of previous raster data is weighted by decreasing percentages.

9. The method of claim 1, wherein the image palette can include multiple colors which are effective for increasing the perception of changes in the resultant raster image compared to a greyscale palette.

10. The method of claim 1, further including a step of determining if the charged particle beam system is in an imaging mode, thereby classifying the frame information as corresponding to an imaging mode operation for imaging a field of view or a subset of the field of view.

11. The method of claim 10, wherein an image corresponding to frame information for the imaging mode operation is displayed in an imaging mode window.

12. The method of claim 11, wherein the raster image is displayed in a raster mode window.

13. The method of claim 12, wherein the imaging mode window is brought to the foreground if the frame information is classified as an imaging mode operation, and the raster mode window is brought to the foreground if the frame information is classified as a raster operation.

14. The method of claim 12, wherein the raster image is scaled and superimposed in the correct location on the imaging mode window.

15. The method of claim 1, wherein steps b) and c) are repeated two or more times for a plurality of regions of interest and a variable number of frames.

16. The method of claim 1, wherein step b) is repeated two or more times for the first region of interest and a variable number of frames and image palettes.

17. The method of claim 15, wherein step c) is executed for only the region of interest with the smallest area.

18. The method of claim 1, further including generating thumbnail data from the raster data by scaling the raster data after one of a predetermined time interval, a predetermined dose increment or a predetermined number of frames, for subsequent storage.

19. The method of claim 18, further including storing one or more of the image palette, a charged particle beam current, a delivered charged particle dose, a rastering time and the endpoint graph data corresponding to the thumbnail data.

20. The method of claim 19, further including a step of displaying the endpoint graph and at least one thumbnail image constructed by applying the image palette to at least one of the thumbnail data, each thumbnail image being cross-referenced to one corresponding intensity value on the endpoint graph such that selecting a value on the endpoint graph causes the nearest cross-referenced thumbnail to be displayed.

21. The method of claim 18, further including a step of constructing a cross-section image by defining a line segment in the plane of the thumbnail data, and generating a row of the cross-section image by analyzing the intensity values along the line segment of each thumbnail datum and stacking each row sequentially from top to bottom, such that the horizontal axis of the cross-section image corresponds to space and the vertical axis corresponds to time or dose.

22. The method of claim 21, wherein the step of analyzing includes one of averaging or integrating the intensity values along a vector perpendicular to the line segment for a predetermined distance on either side of the line segment.

23. The method of claim 21, further including a step of displaying the endpoint graph, at least one thumbnail image constructed by applying a predetermined image palette to at least one of the thumbnail datum, and the cross section image, each thumbnail image being cross-referenced to one corresponding intensity value on the endpoint graph and one row of the cross-section image.

24. The method of claim 23, wherein selecting a point on the endpoint graph causes the nearest cross-referenced thumbnail image to be displayed and the cross-referenced row of the cross-section image to be indicated.

25. The method of claim 23, wherein selecting a row on the cross-section image causes the cross-referenced thumbnail image to be displayed and the cross-referenced point on the endpoint graph to be indicated.

26. The method of claim 1, wherein the first region of interest is set to be an area occupied by at least one raster shape in the frame.

27. The method of claim 1, wherein the first region of interest is set to be a subset of an area occupied by at least one raster shape in the frame.

28. The method of claim 27, wherein the subset is selected to exclude all dwell points within a predetermined distance from a perimeter of the at least one raster shape.

29. The method of claim 28, wherein the at least one raster shape has at least one internal perimeter, the subset being selected to further exclude all dwell points within another predetermined distance from the at least one internal perimeter.

30. The method of claim 27, wherein the first region of interest is set to be a union of the areas occupied by at least two raster shapes overlapping in the frame.

31. The method of claim 30, wherein the first region of interest is further selected to exclude all dwell points within a predetermined distance from a perimeter of the at least one raster shape.

32. The method of claim 1, wherein the second region of interest is set to be the area occupied by at least one raster shape in the frame.

33. The method of claim 1, wherein the second region of interest is set to be a subset of the area occupied by at least one raster shape in the frame.

34. The method of claim 33, wherein the subset is selected to exclude all dwell points within a predetermined distance from a perimeter of the at least one raster shape.

35. The method of claim 34, wherein the at least one raster shape has at least one internal perimeter, the subset being selected to further exclude all dwell points within another predetermined distance from the at least one internal perimeter.

36. The method of claim 33, wherein the second region of interest is set to be a union of the areas occupied by at least two raster shapes overlapping in the frame.

37. The method of claim 36, wherein the second region of interest is further selected to exclude all dwell points within a predetermined distance from a perimeter of the at least one raster shape.

38. The method of claim 1, wherein the information from each frame generated by the CPB system, and CPB system operating parameters are stored for subsequent retrieval and processing according to steps b) and c).

39. The method of claim 1, wherein the step of plotting includes re-scaling the y-axis to a new range which includes all summed dwell point intensity values over the range of the x-axis displayed on the endpoint graph, for increasing ease of perception in determining when changes in the summed dwell point intensity values are occurring.

40. A method for imaging in a charged particle beam system operation involving material modification, comprising:
   a) receiving dwell point information from each frame generated by the CPB system, the information including dwell point intensity values;
   b) processing the dwell point intensity values of a region of interest of a number of frames to derive raster data, mapping the raster data to an image palette and displaying the resultant raster image stretched by a first predetermined factor greater than zero in a first axis and by a second predetermined factor greater than zero in a second axis.

41. The method of claim 40, wherein the first predetermined factor and the second predetermined factor are equal.

42. The method of claim 40, wherein the second predetermined factor is greater than the first predetermined factor.

* * * * *